US007389943B2

(12) United States Patent
Jaworski

(10) Patent No.: US 7,389,943 B2
(45) Date of Patent: Jun. 24, 2008

(54) ELECTROMECHANICAL APPARATUS FOR DISPENSING VOLATILE SUBSTANCES WITH SINGLE DISPENSING MECHANISM AND CARTRIDGE FOR HOLDING MULTIPLE RECEPTACLES

(75) Inventor: Thomas Jaworski, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 407 days.

(21) Appl. No.: 11/170,625

(22) Filed: Jun. 29, 2005

(65) Prior Publication Data
US 2006/0011739 A1    Jan. 19, 2006

Related U.S. Application Data

(60) Provisional application No. 60/583,604, filed on Jun. 30, 2004, provisional application No. 60/670,519, filed on Apr. 12, 2005.

(51) Int. Cl.
*B05B 1/08* (2006.01)
*B05B 9/03* (2006.01)
*B05B 9/00* (2006.01)
*A61M 11/00* (2006.01)

(52) U.S. Cl. .................. 239/102.2; 239/67; 239/304; 239/305; 239/326; 239/338; 261/DIG. 88

(58) Field of Classification Search .............. 239/102.2, 239/67, 304, 305, 326, 338, 34, 44, 45, 47, 239/49, 70, 102.1, 302, 303, 390, 392, 394, 239/396; 261/DIG. 88, DIG. 65; 392/390, 392/394, 395
See application file for complete search history.

(56) References Cited

U.S. PATENT DOCUMENTS 1,204,934 A    11/1916 Burford et al.

(Continued)

FOREIGN PATENT DOCUMENTS

AU    2005101048    2/2006

(Continued)

OTHER PUBLICATIONS

Int'l Search Report dated May 3, 2004 PCT/US2003/36090.

(Continued)

*Primary Examiner*—Darren Gorman

(57) ABSTRACT

An apparatus for dispensing a volatile substance includes an electromechanical dispenser attached to a pivot arm, and a cartridge for holding a plurality of reservoirs each containing a volatile substance. The cartridge is rotatable such that any one of the reservoirs can be positioned in an engagement position, in which the volatile substance can be dispensed. The cartridge has a cam feature consisting of a contoured circumferential surface that alternately rises and falls. The pivot arm operates in tandem with the cam feature such that, when the cartridge is rotated, the dispenser alternately engages and disengages from successive reservoirs, and remains out of the path of motion traversed by the reservoirs as the cartridge rotates from one engagement position to a subsequent engagement position. The electromechanical dispenser may be a piezoelectrically actuated vibratory type liquid atomization apparatus, and the volatile substance may be a fragrance.

22 Claims, 21 Drawing Sheets

U.S. PATENT DOCUMENTS

| | | | |
|---|---|---|---|
| 1,763,374 A | 6/1930 | Schrader | |
| 1,829,714 A | 10/1931 | McElroy et al. | |
| 1,947,752 A | 2/1934 | Benesh | |
| 2,084,682 A | 6/1937 | Guenot | |
| 2,094,161 A | 9/1937 | Paddock | |
| 2,103,609 A | 12/1937 | Bradbum | |
| 2,221,876 A | 11/1940 | Mackin | |
| 2,301,691 A | 11/1942 | Ellinger et al. | |
| 2,555,047 A | 5/1951 | Logue | |
| 2,600,877 A | 6/1952 | Jeffree | |
| 2,608,436 A | 8/1952 | Baughman | |
| 2,686,944 A | 8/1954 | Gubelin | |
| 2,741,004 A | 4/1956 | Williams | |
| 2,905,049 A | 9/1959 | Laube | |
| D191,396 S | 9/1961 | Weber, III | |
| 3,118,610 A | 1/1964 | Techler | |
| 3,172,604 A | 3/1965 | Brock | |
| 3,301,486 A | 1/1967 | Brock | |
| 3,370,571 A | 2/1968 | Knapp | |
| 3,370,951 A | 2/1968 | Knapp | |
| 3,383,178 A | 5/1968 | Dietz | |
| 3,410,488 A | 11/1968 | Sugimura | |
| 3,447,505 A | 6/1969 | Wagner | |
| 3,612,356 A | 10/1971 | McVey | |
| 3,628,829 A | 12/1971 | Heilig | |
| 3,655,135 A | 4/1972 | Altman et al. | |
| 3,711,023 A | 1/1973 | Smith | |
| 3,763,888 A | 10/1973 | Duecker | |
| 3,812,996 A | 5/1974 | Bunnell | |
| 3,864,080 A | 2/1975 | Valbona et al. | |
| 3,917,396 A | 11/1975 | Donohue et al. | |
| 3,972,473 A | 8/1976 | Harrison | |
| 4,006,841 A | 2/1977 | Alticosalian | |
| 4,084,732 A | 4/1978 | Dearling | |
| 4,229,415 A | 10/1980 | Bryson | |
| 4,235,373 A | 11/1980 | Clark | |
| 4,346,059 A | 8/1982 | Spector | |
| 4,391,390 A | 7/1983 | Howard | |
| 4,433,796 A | 2/1984 | Brooks, Jr. | |
| 4,456,176 A | 6/1984 | Agius | |
| 4,545,396 A | 10/1985 | Miller et al. | |
| 4,556,539 A | 12/1985 | Spector | |
| 4,580,721 A | 4/1986 | Coffee et al. | |
| 4,603,030 A | 7/1986 | McCarthy | |
| 4,614,300 A | 9/1986 | Falcoff | |
| 4,629,164 A | 12/1986 | Sommerville | |
| 4,629,604 A | 12/1986 | Spector | |
| 4,680,060 A | 7/1987 | Gupta et al. | |
| 4,695,434 A | 9/1987 | Spector | |
| 4,755,404 A | 7/1988 | Collette | |
| 4,790,479 A | 12/1988 | Matsumoto et al. | |
| 4,804,821 A | 2/1989 | Glucksman | |
| 4,846,403 A | 7/1989 | Mivelaz | |
| 4,852,802 A | 8/1989 | Iggulden et al. | |
| 4,870,991 A | 10/1989 | McMillan et al. | |
| 4,878,615 A | 11/1989 | Losi | |
| 4,881,568 A | 11/1989 | Ho | |
| 4,889,285 A | 12/1989 | Locko | |
| 4,893,615 A | 1/1990 | Khabirova | |
| 4,901,890 A | 2/1990 | Mivelaz | |
| 4,905,112 A | 2/1990 | Rhodes | |
| 4,913,034 A | 4/1990 | Ripple et al. | |
| 4,915,301 A | 4/1990 | Munteanu | |
| 4,917,301 A | 4/1990 | Munteanu | |
| 5,011,632 A | 4/1991 | Yano et al. | |
| 5,021,701 A | 6/1991 | Takahashi et al. | |
| 5,022,585 A | 6/1991 | Burgess | |
| 5,023,020 A | 6/1991 | Machida et al. | |
| 5,038,972 A | 8/1991 | Muderlak et al. | |
| 5,050,798 A | 9/1991 | Sullivan | |
| 5,071,621 A | 12/1991 | Tokuhiro et al. | |
| 5,074,438 A | 12/1991 | Ingram | |
| 5,086,978 A * | 2/1992 | Fertig | 239/305 |
| 5,097,375 A | 3/1992 | Khan | |
| 5,105,133 A | 4/1992 | Yang | |
| 5,111,477 A | 5/1992 | Muderlak | |
| 5,115,975 A | 5/1992 | Shilling | |
| 5,133,498 A | 7/1992 | Sealy et al. | |
| 5,152,397 A | 10/1992 | Mayled | |
| 5,163,616 A | 11/1992 | Bernarducci et al. | |
| 5,167,877 A | 12/1992 | Pai | |
| 5,175,791 A | 12/1992 | Muderlak et al. | |
| 5,178,327 A | 1/1993 | Palamand et al. | |
| 5,186,869 A | 2/1993 | Stumpf et al. | |
| 5,192,342 A | 3/1993 | Baron et al. | |
| 5,193,744 A | 3/1993 | Goldstein | |
| 5,201,025 A | 4/1993 | Landesberg | |
| 5,212,672 A | 5/1993 | Loisch et al. | |
| 5,227,068 A | 7/1993 | Runyon | |
| 5,230,837 A | 7/1993 | Babasade | |
| 5,234,162 A | 8/1993 | Sullivan | |
| 5,314,619 A | 5/1994 | Runyon | |
| 5,314,669 A | 5/1994 | Hamilton | |
| 5,321,669 A | 6/1994 | Thayer et al. | |
| 5,342,584 A | 8/1994 | Fritz et al. | |
| 5,343,747 A | 9/1994 | Rosen | |
| 5,364,027 A | 11/1994 | Kuhn | |
| 5,377,363 A | 1/1995 | Shieh | |
| RE34,847 E | 2/1995 | Muderlak et al. | |
| 5,398,070 A | 3/1995 | Lee | |
| 5,402,517 A | 3/1995 | Gillet et al. | |
| D359,346 S | 6/1995 | Martin | |
| 5,437,410 A | 8/1995 | Babasade | |
| 5,449,117 A | 9/1995 | Muderlak et al. | |
| 5,518,790 A | 5/1996 | Huber et al. | |
| 5,524,609 A | 6/1996 | Krull | |
| 5,534,229 A | 7/1996 | Nomura et al. | |
| 5,565,148 A | 10/1996 | Pendergrass, Jr. | |
| 5,591,409 A | 1/1997 | Watkins | |
| 5,647,052 A | 7/1997 | Patel et al. | |
| 5,658,387 A | 8/1997 | Reardon et al. | |
| 5,660,330 A | 8/1997 | Scott | |
| 5,666,987 A | 9/1997 | Combs | |
| 5,695,692 A | 12/1997 | Kennedy | |
| 5,724,256 A | 3/1998 | Lee et al. | |
| 5,725,472 A | 3/1998 | Weathers | |
| 5,727,186 A | 3/1998 | Shervington et al. | |
| 5,734,590 A | 3/1998 | Tebbe | |
| 5,762,268 A | 6/1998 | Shervington et al. | |
| 5,772,074 A | 6/1998 | Dial et al. | |
| 5,776,561 A | 7/1998 | Lindauer | |
| 5,805,768 A | 9/1998 | Schwartz et al. | |
| 5,810,201 A | 9/1998 | Besse et al. | |
| 5,816,446 A | 10/1998 | Steindorf et al. | |
| 5,832,320 A | 11/1998 | Wittek | |
| 5,881,714 A | 3/1999 | Yokoi et al. | |
| 5,884,808 A | 3/1999 | Muderlak et al. | |
| 5,887,118 A | 3/1999 | Huffman et al. | |
| 5,894,841 A | 4/1999 | Voges | |
| 5,898,475 A | 4/1999 | Martin | |
| 5,899,381 A | 5/1999 | Gordon et al. | |
| 5,899,382 A | 5/1999 | Hayes et al. | |
| 5,908,231 A | 6/1999 | Huff | |
| 5,924,597 A | 7/1999 | Lynn | |
| 5,938,117 A | 8/1999 | Ivri | |
| 5,949,522 A | 9/1999 | Manne | |
| 5,972,290 A | 10/1999 | De Sousa | |
| 5,975,675 A | 11/1999 | Kim | |
| 6,000,658 A | 12/1999 | McCall, Jr. | |
| 6,003,727 A | 12/1999 | Marshall | |
| 6,013,231 A | 1/2000 | Zaunbrecher et al. | |
| 6,039,212 A | 3/2000 | Singh | |
| 6,044,202 A | 3/2000 | Junkel | |
| 6,053,738 A | 4/2000 | Ivey, Jr. | |

| | | | | | | |
|---|---|---|---|---|---|---|
| 6,123,935 | A | 9/2000 | Wefler et al. | 6,912,355 B2 | 6/2005 | Vieira |
| 6,136,277 | A | 10/2000 | Nardini | 6,913,208 B2 * | 7/2005 | Tabata et al. ................ 239/305 |
| 6,189,810 | B1 | 2/2001 | Nerushai et al. | 6,913,733 B2 | 7/2005 | Hardy et al. |
| 6,196,218 | B1 | 3/2001 | Voges | 6,921,024 B2 | 7/2005 | Donnelly et al. |
| 6,231,032 | B1 | 5/2001 | Ivey, Jr. | 7,011,795 B2 | 3/2006 | Thompson et al. |
| 6,234,455 | B1 | 5/2001 | Wittek | 7,021,494 B2 | 4/2006 | Mazooji et al. |
| 6,241,944 | B1 | 6/2001 | Budman | 7,223,166 B1 | 5/2007 | Wiseman, Sr. et al. |
| 6,254,065 | B1 | 7/2001 | Ehrensperger et al. | 2001/0048037 A1 | 12/2001 | Bell et al. |
| 6,254,248 | B1 | 7/2001 | McAuley et al. | 2002/0018181 A1 | 2/2002 | Manne |
| 6,279,836 | B1 | 8/2001 | Toetschinger et al. | 2002/0066798 A1 | 6/2002 | Laudamiel-Pellet et al. |
| 6,293,474 | B1 | 9/2001 | Helf et al. | 2002/0068009 A1 | 6/2002 | Laudamiel-Pellet et al. |
| 6,296,196 | B1 | 10/2001 | Denen et al. | 2002/0068010 A1 | 6/2002 | Laudamiel-Pellet et al. |
| D451,990 | S | 12/2001 | Millet | 2002/0114744 A1 | 8/2002 | Chiao et al. |
| 6,328,287 | B2 | 12/2001 | Wittek | 2002/0158351 A1 | 10/2002 | Wohrle |
| 6,338,818 | B2 | 1/2002 | Budman | 2002/0159916 A1 | 10/2002 | Whitby et al. |
| 6,341,732 | B1 | 1/2002 | Martin et al. | 2003/0006303 A1 | 1/2003 | Ivey et al. |
| 6,357,726 | B1 | 3/2002 | Watkins | 2003/0102384 A1 | 6/2003 | Walter et al. |
| 6,371,451 | B1 | 4/2002 | Choi | 2003/0107139 A1 | 6/2003 | Wohrle |
| 6,382,522 | B2 | 5/2002 | Tomkins et al. | 2003/0138241 A1 | 7/2003 | Pedrotti et al. |
| 6,390,453 | B1 | 5/2002 | Frederickson et al. | 2003/0164557 A1 | 9/2003 | Chung et al. |
| 6,406,004 | B1 | 6/2002 | Ude | 2003/0168524 A1 | 9/2003 | Hess et al. |
| 6,409,093 | B2 | 6/2002 | Ulczynski et al. | 2003/0168751 A1 | 9/2003 | Bartsch et al. |
| 6,421,944 | B1 | 7/2002 | Klebes et al. | 2003/0175148 A1 | 9/2003 | Kvietok |
| 6,439,474 | B2 | 8/2002 | Denen | 2003/0192959 A1 | 10/2003 | Hess et al. |
| D463,437 | S | 9/2002 | Bush et al. | 2003/0206834 A1 | 11/2003 | Chiao et al. |
| 6,446,583 | B2 | 9/2002 | Vieira | 2004/0007787 A1 | 1/2004 | Kvietok et al. |
| 6,448,219 | B1 | 9/2002 | Cooper | 2004/0009103 A1 | 1/2004 | Westring |
| 6,450,419 | B1 * | 9/2002 | Martens et al. .......... 239/102.1 | 2004/0016818 A1 | 1/2004 | Murdell et al. |
| D464,130 | S | 10/2002 | Denham et al. | 2004/0028551 A1 | 2/2004 | Kvietok et al. |
| 6,487,367 | B2 | 11/2002 | Vieira | 2004/0033067 A1 | 2/2004 | He et al. |
| 6,501,906 | B2 | 12/2002 | Vieira | 2004/0033171 A1 | 2/2004 | Kvietok et al. |
| 6,502,762 | B2 | 1/2003 | Tuttobene, Jr. | 2004/0071456 A1 | 4/2004 | Levine et al. |
| 6,505,759 | B2 | 1/2003 | Holyfield | 2004/0131509 A1 | 7/2004 | He et al. |
| 6,511,531 | B1 | 1/2003 | Cartellone | 2004/0195372 A1 | 10/2004 | Yoshikawa et al. |
| 6,520,826 | B2 | 2/2003 | Spector | 2004/0217188 A1 | 11/2004 | McEwen |
| 6,533,193 | B2 | 3/2003 | White | 2004/0217197 A1 | 11/2004 | Mazooji et al. |
| 6,536,746 | B2 | 3/2003 | Watkins | 2004/0223871 A1 | 11/2004 | Woo et al. |
| 6,542,442 | B2 | 4/2003 | Kaslon | 2004/0223891 A1 | 11/2004 | Brown |
| 6,554,203 | B2 | 4/2003 | Hess et al. | 2004/0223943 A1 | 11/2004 | Woo et al. |
| 6,556,272 | B1 | 4/2003 | Du et al. | 2004/0241053 A1 | 12/2004 | Thompson et al. |
| 6,563,091 | B2 | 5/2003 | Vieira | 2004/0247301 A1 | 12/2004 | Yip et al. |
| 6,568,659 | B2 | 5/2003 | Hugon | 2004/0265164 A1 | 12/2004 | Woo et al. |
| 6,569,387 | B1 | 5/2003 | Furner et al. | 2005/0001337 A1 | 1/2005 | Pankhurst et al. |
| 6,581,915 | B2 | 6/2003 | Bartsch et al. | 2005/0028819 A1 | 2/2005 | Manne |
| 6,584,633 | B2 | 7/2003 | Chute et al. | 2005/0147523 A1 | 7/2005 | Laudamiel-Pellet et al. |
| 6,592,104 | B2 | 7/2003 | Cox | 2005/0147539 A1 | 7/2005 | Laudamiel-Pellet et al. |
| 6,602,475 | B1 | 8/2003 | Chiao | 2005/0161522 A1 | 7/2005 | Kvietok et al. |
| 6,603,924 | B2 | 8/2003 | Brown et al. | 2005/0201944 A1 | 9/2005 | Kvietok et al. |
| 6,610,254 | B1 | 8/2003 | Furner et al. | 2005/0211790 A1 | 9/2005 | Kvietok et al. |
| 6,619,559 | B2 | 9/2003 | Wohrle | 2005/0214158 A1 | 9/2005 | Kvietok et al. |
| 6,654,664 | B1 | 11/2003 | Chiao | 2006/0018786 A1 | 1/2006 | Tolman et al. |
| 6,661,967 | B2 | 12/2003 | Levine et al. | 2006/0018803 A1 | 1/2006 | Kvietok et al. |
| 6,706,988 | B1 | 3/2004 | Helf et al. | 2006/0067859 A1 | 3/2006 | Laudamiel-Pellet et al. |
| 6,712,287 | B1 | 3/2004 | Le Pesant et al. | 2006/0097065 A1 | 5/2006 | Kvietok et al. |
| 6,713,024 | B1 | 3/2004 | Arnell et al. | 2006/0097066 A1 | 5/2006 | Kvietok et al. |
| 6,714,725 | B2 | 3/2004 | Grone et al. | 2006/0193611 A1 | 8/2006 | Ballersteros et al. |
| 6,728,478 | B2 | 4/2004 | Cox et al. | | | |
| 6,769,905 | B2 | 8/2004 | Gray et al. | | FOREIGN PATENT DOCUMENTS | |
| 6,783,117 | B2 | 8/2004 | Wohrle | | | |
| 6,790,011 | B1 | 9/2004 | Le Pesant et al. | CA | 2222838 | 1/1997 |
| 6,790,408 | B2 | 9/2004 | Whitby et al. | DE | 199 38 405 | 2/2001 |
| 6,792,199 | B2 | 9/2004 | Levine et al. | EP | 0295129 A1 | 12/1988 |
| 6,793,149 | B2 | 9/2004 | Schramm et al. | EP | 0 714 709 | 6/1996 |
| D497,288 | S | 10/2004 | McGuyer | EP | 1 108 358 | 6/2001 |
| 6,802,460 | B2 | 10/2004 | Hess et al. | EP | 1 195 169 | 4/2002 |
| 6,803,987 | B2 | 10/2004 | Manne | EP | 1 247 446 | 10/2002 |
| 6,810,204 | B2 | 10/2004 | Grone et al. | EP | 1 247 447 | 10/2002 |
| 6,834,847 | B2 | 12/2004 | Bush et al. | EP | 1 184 083 | 3/2003 |
| 6,842,218 | B1 | 1/2005 | Manne | EP | 1 303 316 | 4/2003 |
| 6,843,430 | B2 * | 1/2005 | Boticki et al. ............ 239/102.1 | EP | 1 303 317 | 4/2003 |
| 6,859,615 | B2 | 2/2005 | Yip et al. | EP | 1 303 318 | 4/2003 |
| 6,871,794 | B2 | 3/2005 | McEwen | EP | 1 303 319 | 4/2003 |
| 6,896,196 | B2 | 5/2005 | Vieira | EP | 1 469 131 | 10/2004 |

| | | |
|---|---|---|
| GB | 2 253 732 | 9/1992 |
| GB | 2 401 047 | 11/2004 |
| GB | 2 401 790 | 11/2004 |
| GB | 2418859 A | 4/2006 |
| JP | 04-024029 | 1/1992 |
| JP | 40-4267740 | 9/1992 |
| JP | 40-4354950 | 12/1992 |
| JP | 06-320083 | 11/1994 |
| JP | 40-8336578 | 12/1996 |
| JP | 11-000391 | 1/1999 |
| WO | WO 00/12143 | 3/2000 |
| WO | WO 00/53301 | 9/2000 |
| WO | WO 00/60486 | 10/2000 |
| WO | WO 00/60489 | 10/2000 |
| WO | WO 02/09772 A3 | 2/2002 |
| WO | WO 02/09773 A3 | 2/2002 |
| WO | WO 02/09776 A3 | 2/2002 |
| WO | WO 02/09779 | 2/2002 |
| WO | WO 02/32472 | 4/2002 |
| WO | WO 02/32472 A1 | 4/2002 |
| WO | WO 03/027220 A1 | 4/2002 |
| WO | WO 03/068412 | 8/2003 |
| WO | WO 03/098971 | 11/2003 |
| WO | WO 03/099458 A2 | 12/2003 |
| WO | WO 03/102291 | 12/2003 |
| WO | WO 03/105652 | 12/2003 |
| WO | WO 04/007008 | 1/2004 |
| WO | WO 04/009142 | 1/2004 |
| WO | WO 04/011836 | 2/2004 |
| WO | WO 2004/043502 A1 | 5/2004 |
| WO | WO 04/071935 | 8/2004 |
| WO | WO 2004/093927 A1 | 11/2004 |
| WO | WO 2004/093928 A2 | 11/2004 |
| WO | WO 2004/093929 A2 | 11/2004 |
| WO | WO 2004/105813 A1 | 12/2004 |
| WO | WO 2004/105814 A1 | 12/2004 |
| WO | WO 2004/105815 A2 | 12/2004 |
| WO | WO 2004/105878 A1 | 12/2004 |
| WO | WO 05/011761 | 2/2005 |
| WO | WO 2006/105347 | 10/2006 |

OTHER PUBLICATIONS

Int'l Search Report & Written Opinion dated Nov. 15, 2005 PCT/US2005/023211.
Int'l Search Report and Written Opinion dated Sep. 1, 2006 PCT/US/2006/013600.
Yankee Candle Web Page http://www.yankeecandle.com/cgi-bin/ycbvp/product)detail.jsp?oid=3001476 1 page, printed May 15, 2007.
SCJ Create a Scent Web Page http://www.glade.com/glade-plug-ins/ 3 pages, printed May 16, 2007.

* cited by examiner ated vibratory type liquid atomization apparatus for emitting a fragrance. More particularly, it relates to such a dispenser having a single dispensing mechanism, such as a single atomization device, and a carousel that holds multiple receptacles each containing a volatile fragrant substance, the single atomization device being capable of engaging any of the receptacles by means of movement of the receptacles, such as by rotation of the carousel relative to the atomization device.

ELECTROMECHANICAL APPARATUS FOR DISPENSING VOLATILE SUBSTANCES WITH SINGLE DISPENSING MECHANISM AND CARTRIDGE FOR HOLDING MULTIPLE RECEPTACLES

CROSS-REFERENCE TO RELATED APPLICATIONS

This application claims the benefit of, and incorporates by reference, U.S. Provisional Patent Application No. 60/583,604, filed Jun. 30, 2004, and U.S. Provisional Patent Application No. 60/670,519, filed Apr. 12, 2005.

BACKGROUND OF THE INVENTION

1. Field of the Invention

This invention relates to an electromechanical dispenser for dispensing a volatile substance, such as a piezoelectrically actuated vibratory type liquid atomization apparatus for emitting a fragrance. More particularly, it relates to such a dispenser having a single dispensing mechanism, such as a single atomization device, and a carousel that holds multiple receptacles each containing a volatile fragrant substance, the single atomization device being capable of engaging any of the receptacles by means of movement of the receptacles, such as by rotation of the carousel relative to the atomization device.

2. Description of the Related Art

Electromechanical dispensers for dispensing a volatile substance, based on a variety of operating principles or technologies, are known in the art. For example, such a dispenser may comprise a heating element for heating the volatile substance to promote vaporization and a fan or blower to generate a flow of air to direct the evaporate out of the device into the surrounding environment. Examples of dispensers of this type are described in U.S. Pat. No. 6,619,559 and U.S. Patent Application Publication Nos. 2003/0107139 and 2002/0066798. The heating element may be omitted from such a device, as shown, for example, in U.S. Pat. No. 6,713,024, or it may be replaced by an alternative means to promote evaporation, such as a diffusion screen, as described in U.S. Pat. No. 6,568,659. The fan or blower may also be omitted, as described in U.S. Pat. No. 5,805,768, according to which a heated aromatic material emanates from the dispenser into the environment upon opening of an otherwise sealed receptacle containing the material. Alternatively, U.S. Pat. No. 6,357,726 describes a variation to the fan or blower, namely, a bolus generator that delivers a pulse of air to eject a scent ring, similar to a smoke ring exhaled by a smoker. Another type of electromechanical dispenser is an ultrasonic device such as that described in U.S. Pat. No. 5,011,632, in which a fragrance solution, in the form of a thin liquid membrane formed on a vibrating surface, is vaporized by being made to absorb the energy of ultrasonic waves. Dispensers of volatile substances based on other operating principles, as well as other variations in dispensers of any given type, are known to those of ordinary skill in the art.

Regardless of the operating principle of the dispenser, it is not uncommon to include in the dispenser elements for automation and control such as a motor, a controller, and the like, to control such factors as the frequency and duration of emissions of the volatile substance, which in turn determine the intensity of the emitted fragrance. While it is of course possible to design a dispenser devoid of electrical or even mechanical components, inasmuch as many volatile substances of interest will spontaneously vaporize, in practice, such technologically primitive devices generally exhibit a variety of performance limitations, particularly with respect to the ability to vary the modes of, or otherwise control, operation of the device. U.S. Pat. Nos. 5,605,692 and 2,103,609, U.S. Patent Application Publication No. 2002/0058595, and UK Patent Application Publication GB 2 256 589 offer examples of simple devices of this sort having limited or no mechanical features.

An example of a piezoelectrically actuated vibratory type liquid atomization apparatus is described in U.S. Pat. No. 6,843,430, which is assigned to the assignee of this invention and incorporated herein by reference. As described therein, a piezoelectrically actuated vibratory type liquid atomization apparatus comprises a piezoelectric actuating element coupled to a liquid atomization plate. The piezoelectric actuating element vibrates the liquid atomization plate, in response to alternating electrical voltages applied to the actuating element. The vibration of the plate causes atomization of a liquid supplied to it by a liquid delivery system, which is arranged to deliver the liquid while the atomization plate is being vibrated. An electrical circuit is provided to supply the alternating electrical voltages to conductive elements that are arranged to be in electrical contact with opposite sides of the actuating element to apply the alternating voltages across the actuating element. The conductive elements may also serve to support the actuating element and the liquid atomization plate in a housing that contains the device.

Other examples of piezoelectric vibratory type liquid atomization apparatuses of a variety of types are described in U.S. Pat. Nos. 6,450,419, 6,085,740 and 4,301,093, and published European Patent Application EP 0 897 755.

In regard to fragrance dispensing devices, it is known that if a user is continually exposed to the same odor or fragrance, the user's olfactory sense can become desensitized to the scent. This phenomenon is referred to as "fragrance fatigue." One way to overcome fragrance fatigue is to provide a dispenser capable of emitting different fragrances. Thus, many of the above-mentioned documents suggest a device having multiple receptacles for containing volatile substances, respectively, such that the device can hold and emit multiple, different fragrances. The different receptacles may be stationary, such as in the case of U.S. Pat. No. 6,357,726, or they may be movable, e.g., radially disposed on a tray or cartridge that may be rotated to align a given receptacle with a heater and/or an exit hole, or the like, for emission of the substance in the receptacle, such as are shown in U.S. Pat. Nos. 5,805,768, 5,605,692 and 2,103,609, U.S. Patent Application Publication Nos. 2002/0066798 and 2003/0107139, and UK Patent Application Publication GB 2 256 589. While in some cases a single dispensing mechanism (e.g., a heater and/or an exit hole) serves all of the multiple receptacles, in other cases, each of the multiple receptacles is provided with its own dispensing mechanism, in part or in whole.

Pending PCT Application No. PCT/US03/36090 (now published as International Publication No. WO 2004/043502 A1), filed Nov. 10, 2003, assigned to the assignee of this invention and incorporated herein by reference, teaches an apparatus including multiple volatile substance reservoirs, each of which is provided with its own piezoelectrically actuated atomization device. While such an apparatus is capable of providing enhanced performance, for example, in the way of a variety of modes, fragrance combinations, and control or programming, the provision of multiple atomization devices significantly increases the cost of manufacture. Thus, there remains a need for a compact piezoelectric atomization apparatus, or other type of electromechanical dispenser, capable of dispensing a variety of volatile substances with some degree of operational flexibility, that can be operated by a user in a highly convenient, simple manual fashion but that can also be provided with a degree of automation and programming control, and that can be manufactured, and hence sold, at a low cost.

SUMMARY OF THE INVENTION

The present invention provides a compact electromechanical dispenser that is capable of dispensing a variety of volatile substances with a significant degree of operational flexibility, subject to the control of a user, that can be operated in a highly convenient, simple manual fashion and can also be provided with the capability of operating in an automated manner, and that can be manufactured at a low cost. Specifically, the present invention provides an electromechanical dispenser of a volatile substance having a cartridge holding multiple receptacles for containing volatile substances, respectively, and a single dispensing mechanism that can be engaged with any of the receptacles to dispense the volatile substance contained therein. According to the invention, the receptacles can be moved, for example, by rotation of the cartridge holding the receptacles, such that any individual receptacle can be brought into a dispensing position in which the volatile substance can be dispensed, while the other receptacles are kept in non-dispensing positions. A cam feature is provided whereby, as the cartridge is rotated in order to disengage a first receptacle from the dispensing mechanism and engage a second receptacle with the dispensing mechanism, the rotation of the cartridge causes the dispensing mechanism to disengage from the first receptacle, to be kept out of the path of motion of the receptacles during rotation, and to engage the second receptacle when the second receptacle is properly aligned with the dispensing mechanism. Also provided are manual rotation levers for rotating the cartridge, which levers also provide feedback to the user as to whether the receptacles are properly aligned (the receptacles are properly aligned when any one receptacle is properly aligned with the dispensing mechanism). By providing an apparatus capable of holding multiple receptacles, integrated, via a cam feature, with a single dispensing mechanism, the present invention is able to keep manufacturing costs to a minimum while yet providing ample operational flexibility (including the ability to dispense a variety of volatile substances) in a convenient, simple, user-friendly format.

The dispensing mechanism according to the present invention may be a piezoelectrically actuated vibratory type liquid atomization device for dispensing a fragrance.

According to a first aspect, the present invention provides an apparatus for dispensing a volatile substance, comprising an electromechanical dispenser for dispensing a volatile substance, a cartridge for holding a plurality of reservoirs, each reservoir for containing a volatile substance to be dispensed, the cartridge being rotatable so as to position any one of the reservoirs in an engagement position in which the one reservoir is engaged with the dispenser in such a manner that the volatile substance in the one reservoir can be dispensed, and a pivot arm for alternately disengaging a reservoir from the dispenser and engaging a successive reservoir with the dispenser during rotation of the cartridge.

The pivot arm causes the dispenser to engage any given reservoir only when the cartridge has been rotated to an engagement position for that reservoir. The pivot arm maintains a state of disengagement, during rotation of the cartridge from one engagement position to a subsequent engagement position.

The state of disengagement is a state in which the dispenser is kept out of the path of motion, specifically, above the path of motion, traversed by the reservoirs as the cartridge is rotated.

The cartridge comprises a cam feature such that, when the cartridge rotates, the pivot arm causes the dispenser to alternately disengage and engage successive reservoirs. The cam feature comprises a cut-away tubular portion having on a longitudinal end thereof a circumferential cross-sectional surface that alternately rises and falls along the circumference. The pivot arm is connected to the dispenser, and the pivot arm abuts the circumferential cross-sectional surface of the cut-away tubular portion such that, when the cartridge is rotated, the pivot arm alternately rises and falls, causing the dispenser to move alternately between a disengagement position and an engagement position.

According to a second aspect of the present invention, the electromechanical dispenser comprises an atomizer assembly comprising an atomization plate and a piezoelectric actuator coupled with the atomization plate to vibrate the atomization plate, thereby atomizing liquid supplied to the atomization plate, and the engagement position is a position in which a reservoir can be engaged with the atomizer assembly in such a manner that the liquid in the reservoir can be supplied to the atomization plate.

Each of the reservoirs includes or is coupled with a liquid delivery member, which may be a wick. By virtue of the alternately rising and falling circumferential cross-sectional surface, the atomizer assembly is maintained at a position above the liquid delivery member of a next-to-be engaged reservoir, before the atomizer assembly engages the next-to-be engaged reservoir, and the atomizer assembly drops down upon the liquid delivery member to engage the next-to-be engaged reservoir, whereby collision, improper engagement and non-engagement of the liquid delivery member with the atomizer assembly, due to vertical misalignment therebetween, are prevented.

According to a third aspect of the present invention, the apparatus according to either the first aspect or the second aspect further comprises a housing, the housing comprising retention snaps for removably retaining the cartridge in the housing in such a manner as to permit rotation of the cartridge.

According to a fourth aspect of the present invention, the apparatus according to any of the first, second or third aspects further comprises at least one handle for rotating the cartridge. The at least one handle may be provided on the cartridge.

According to a fifth aspect of the present invention, the apparatus according to the fourth aspect is provided, wherein the housing has a circumferential surface provided with at least one concave portion, and the at least one handle is provided with a convex portion that fits into the concave portion. As the cartridge is rotated, the concave portion is rotationally brought into alignment with the convex portion at the same time as one of the reservoirs is brought into an engagement position. The aligning of the concave portion with the convex portion thus provides visual, auditory and/or tactile feedback to a user of the apparatus that one of the reservoirs is in an engagement position.

According to a sixth aspect of the present invention, the apparatus according to any of the aforementioned aspects is provided, wherein the housing comprises an exit port for releasing the volatile substance from the dispenser to the atmosphere outside of the apparatus.

According to a seventh aspect of the present invention, the apparatus according to any of the aforementioned aspects further comprises an adjustment lever for adjusting the amount of the volatile substance dispensed, the frequency of the dispensing periods, and/or the duration of the dispensing periods.

According to an eighth aspect of the present invention, the apparatus according to the fifth aspect and also according to the sixth and/or seventh aspects is provided, wherein the exit port and/or the adjustment lever is disposed in alignment, along the circumference of the housing, with the dispenser and with one of the concave portions.

DETAILED DESCRIPTION OF THE PREFERRED EMBODIMENTS

Figure 1:
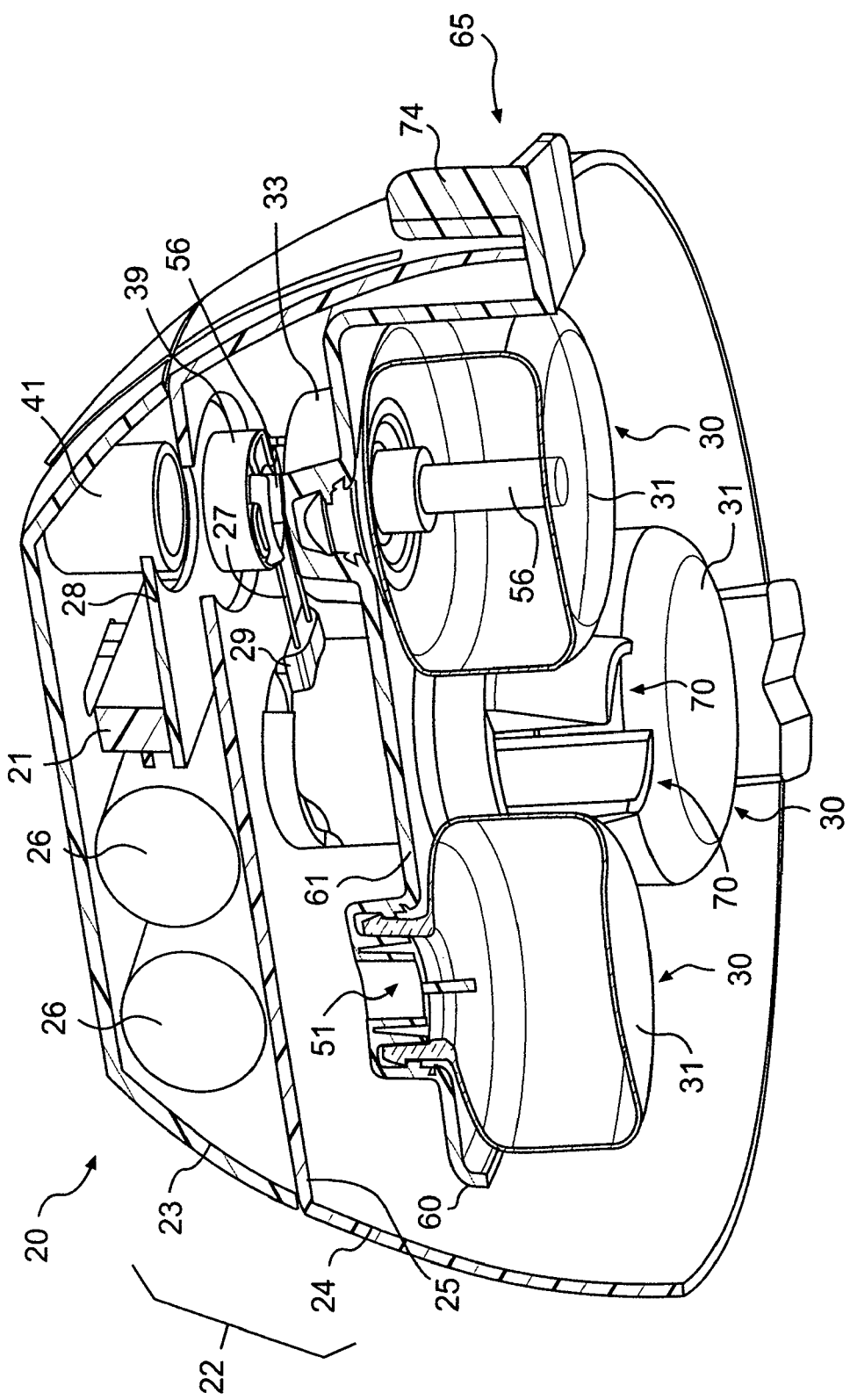
FIG. 1 is a cut-away perspective view of an atomization apparatus embodying the invention, showing a state in which an atomizer assembly is engaged with a reservoir assembly.

The structure and operation of an electromechanical dispenser according to a preferred embodiment of the present invention will be explained with reference to the accompanying drawings. The reader is directed initially to FIGS. 1, 2, 8A and 8B. According to a preferred embodiment, the electromechanical dispenser is a piezoelectrically actuated vibratory type liquid atomization apparatus 20 generally comprising an atomizer assembly 34 (see FIGS. 8A and 8B) and a cartridge 60 holding a plurality of reservoir assemblies 30. The atomizer assembly 34 comprises a piezoelectric actuator element 35 and an orifice plate 37. Each reservoir assembly 30 includes a liquid container 31 containing fluid and a wick 56. (The liquid container 31 or the reservoir assembly 30 may be referred to as a receptacle or a reservoir.) The cartridge 60 can be moved, e.g., rotated, so as to place any reservoir assembly 30 in engagement with the atomizer assembly 34. When a given reservoir assembly 30 is engaged with the atomizer assembly 34, the wick 56 can instantaneously deliver fluid to the orifice plate 37.

As shown in FIG. 1, according to a preferred embodiment of the present invention, the atomization apparatus 20 comprises a housing 22 formed as a hollow plastic shell. A horizontal platform 25 extends across the interior of the housing 22, dividing the housing into an upper portion 23 and a lower portion 24. (The terms "upper," "lower" and the like used herein are to be taken as being relative to the dispenser as disposed in its intended normal operating position, shown in FIG. 1.) One or more batteries 26 are supported on the platform 25 inside the housing 22. Support prongs, stays, or the like (not illustrated), may be employed to keep the batteries in position. In addition, a printed circuit board 28 is supported by a support element 21 that extends downwardly from the top of the upper portion 23 of the housing 22. Appropriate electrical connections are made between the batteries 26 and the circuit board 28 and between the circuit board 28 and the atomizer assembly 34.

The reservoir assembly 30 comprises a liquid container 31 for holding a liquid to be atomized, a plug 33, which closes the top of the container, and the wick 56. The wick 56 extends from inside the liquid container 31, near its bottom, upward through a central cylindrical aperture 51 at the top of the plug 33, to a location outside of and above the liquid container 31. The wick 56 has longitudinally extending capillary passages (not shown) for drawing liquid up from within the liquid container 31 to the upper end of the wick 56. The plug 33 includes the walls 52 of the aperture 51 and an annular sheath portion 53 concentric with the aperture walls 52 (see FIG. 2). The entire plug 33, including the annular sheath portion 53, the aperture walls 52, and a valley portion between the annular sheath portion 53 and the aperture walls 52, is preferably integrally formed as a single member. Preferably, also, the plug 33 is formed as an integral part of a platform 61 of the cartridge 60. The aperture walls 52 serve, together with a collar 102 (described below), to retain the wick 56 in position, in particular, to retain the wick 56 in alignment with the orifice plate 37 of the atomizer assembly 34 when the liquid container 31 is engaged with the atomizer assembly 34. During engagement with the atomizer assembly 34, the wick 56 delivers liquid by capillary action from within the liquid container 31 to the atomizer assembly 34.

Figure 2:
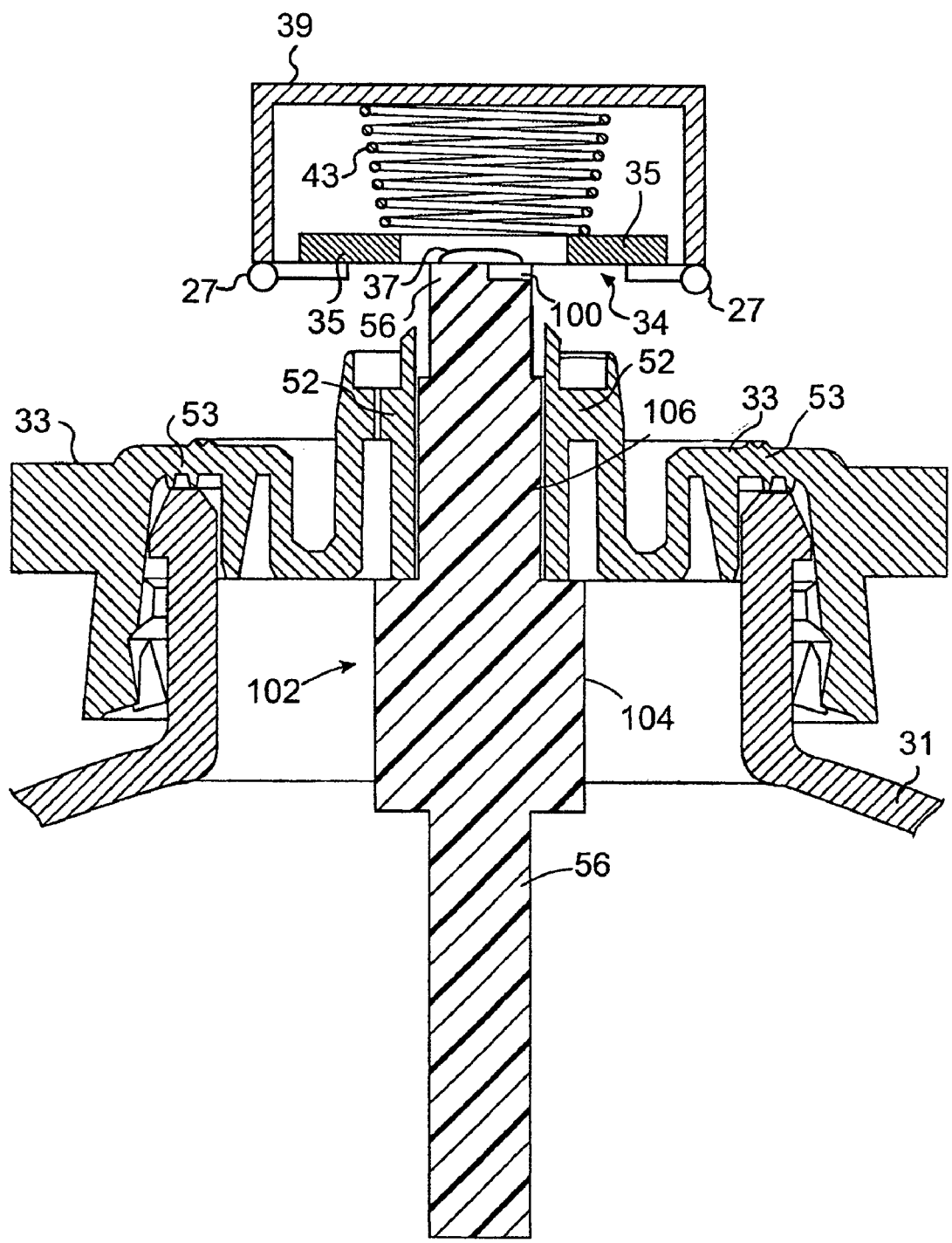
FIG. 2 is an enlarged fragmentary cross-section, taken in elevation, of the upper portion of a reservoir assembly together with an arrangement of the atomizer assembly that may be used in the atomization apparatus of FIG. 1.
Figure 3:
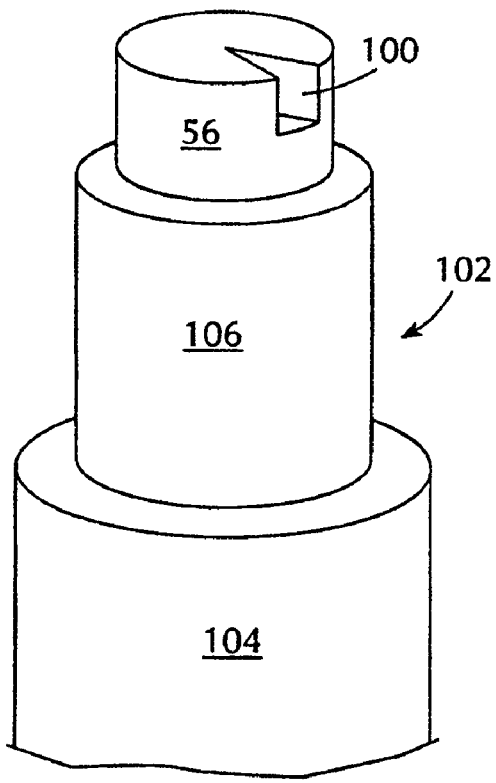
FIG. 3 is a perspective view of the upper portions of a wick and collar that form part of the reservoir assembly of FIG. 2.
Figure 4:
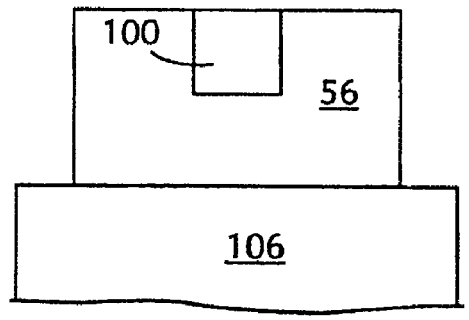
FIG. 4 is an enlarged elevational view of the upper portion of the wick of FIG. 3.

The wick 56 includes an attachment assembly for securing the wick 56 to the plug 33. While the attachment assembly may be a separate piece affixed to the wick 56, it is preferably formed integrally with the wick 56. As shown in FIG. 2, the attachment assembly includes the collar 102 having a lower segment 104 of a relatively large diameter and an upper segment 106 of a relatively small diameter. The top of the lower segment 104 contacts the plug 33 to prevent the wick 56 from moving out of the liquid container 31. The upper segment 106 frictionally fits into the aperture 51 of the plug 33. As noted, the collar 102 together with the aperture walls 52 serve to ensure proper positioning of the wick 56 with respect to the atomizer assembly 34.

While the plug 33 may be constructed to allow removal and replacement of the liquid container 31 from the cartridge 60, it is contemplated that in typical use of the apparatus, a user would replace the cartridge 60, as necessary, rather than replacing individual liquid containers 31.

While the apparatus is contemplated to be used to dispense at least fragrances, it will be appreciated by those of ordinary skill in the art that it could as well be used to dispense other volatile substances including, but not limited to, water, air sanitizer, disinfectant, insect repellent, and insecticide.

When the apparatus is used to dispense fragrances, for example, each of the individual liquid containers 31 may contain a different fragrant substance. The different fragrances may be selected from a group of fragrances having a common theme. For example, three different citrus scents (e.g., lime, lemon and tangerine) could be used for the three liquid containers 31. Since the user can select from among different scents, changing the emitted fragrance and adjusting the intensity level as desired, the apparatus serves to reduce the likelihood that fragrance fatigue will occur. The user may also purchase different cartridges, wherein each cartridge has multiple scents based on a common theme. In this way, the user can choose a themed group of aromas to create an atmosphere that is appropriate to a particular type of event or social gathering, or to a room or other space designated for a particular type of social function. As new scents and scent themes are developed, the apparatus can easily accommodate them, and thus the apparatus is in this respect easily upgradeable over time.

The support of the atomizer assembly 34 in the housing 22 will be explained with reference additionally to FIGS. 20-24. The atomizer assembly 34, housed in its own housing 39, is supported below the platform 25 of the apparatus housing 22 and above the plug 33 in cantilever fashion by means of a resilient, elongated wire-like support 27, which is connected to one end of a pivot arm 29. The other end of the pivot arm 29 is provided with an axle 12 for pivoting. The two ends of the axle 12 are fitted into two holes 13 (see FIGS. 22-24), respectively, formed in a cylindrical portion 14 that extends downward from the platform 25 of the housing 22. (The cylindrical portion 14 has a cut-out portion 15 to accommodate the pivot arm 29 as it extends from the support 27 to the axle 12.) The axle 12 can rotate in the holes 13, whereby the pivot arm 29 can pivot up and down about a pivot point 29a (see FIGS. 13 and 14). The range of rotation of the axle 12, and hence the pivoting range of the pivot arm 29, is limited, below, by the bottom of the cut-out portion 15, and, above, by the ceiling of the platform 25, at the top of the cut-out portion 15. By this arrangement, the assembly comprising the pivot arm 29 and the support 27 resiliently supports the atomizer assembly 34 and its housing 39, and connects the atomizer assembly 34 to the apparatus housing 22 in such a manner that the atomizer assembly 34 can be pivoted up and down. The applicability of the pivoting feature will be explained later.

The atomizer assembly housing 39 has openings in its top and bottom aligned with the orifice plate 37. The wick 56 enters the bottom opening of the atomizer assembly housing 39. The top and bottom openings of the atomizer assembly housing 39 allow liquid to flow up from the wick 56 to the lower surface of the orifice plate 37 and allow droplets to be ejected from the upper surface of the orifice plate 37 to the outside of the apparatus via the exit port 41. The housing 39 also serves to control the flow of liquid so as to prevent undesired side splattering of liquid droplets. The top opening of the atomizer assembly housing 39 is shaped to provide a nozzle effect that directs the flow of the atomized liquid up and out of the apparatus 20 in the form of a cloud.

Figure 8A:
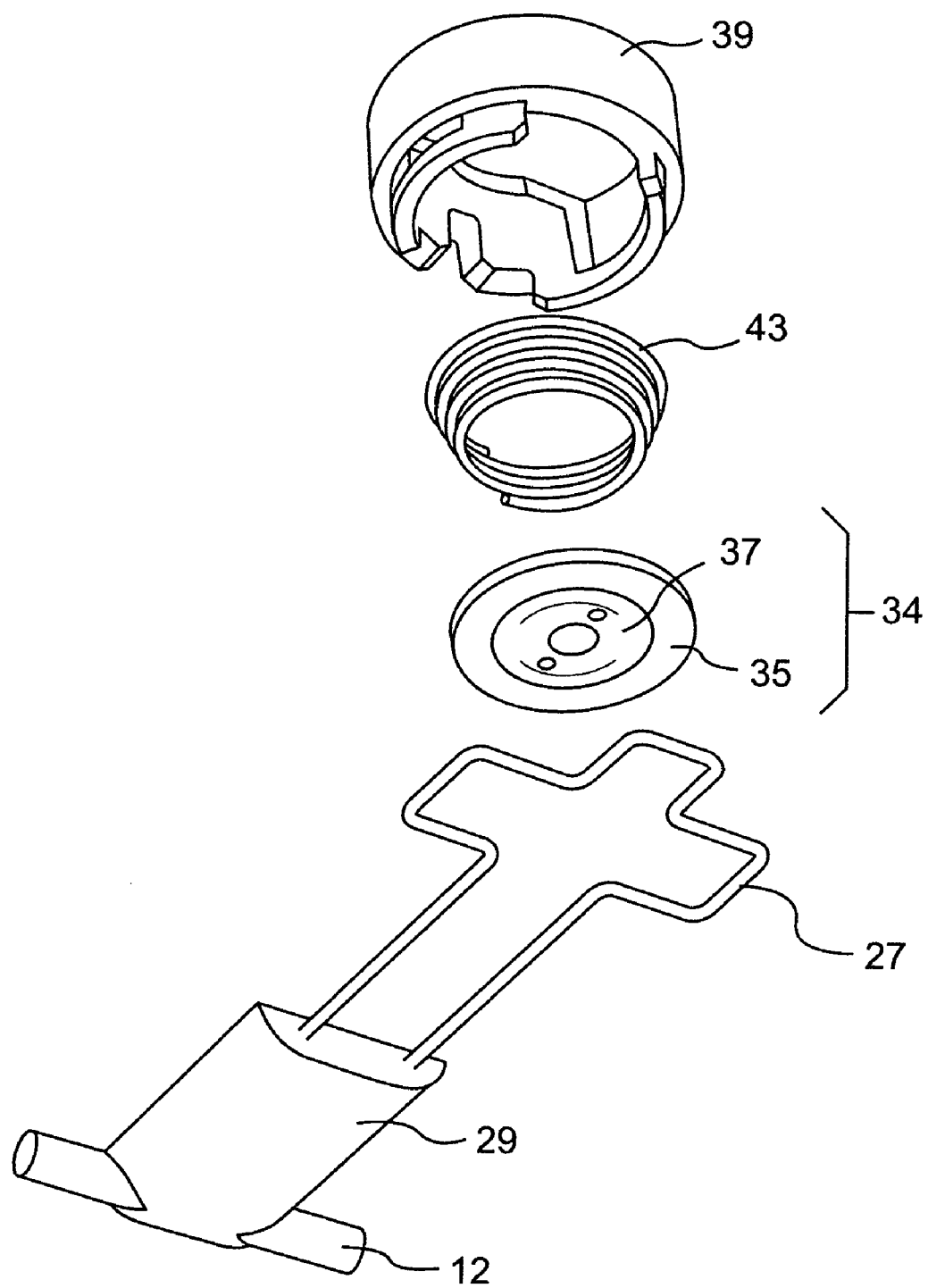
FIGS. 8A and 8B are exploded perspective views of components of the atomizer assembly and its support, as seen from below and from above, respectively.
Figure 8B:
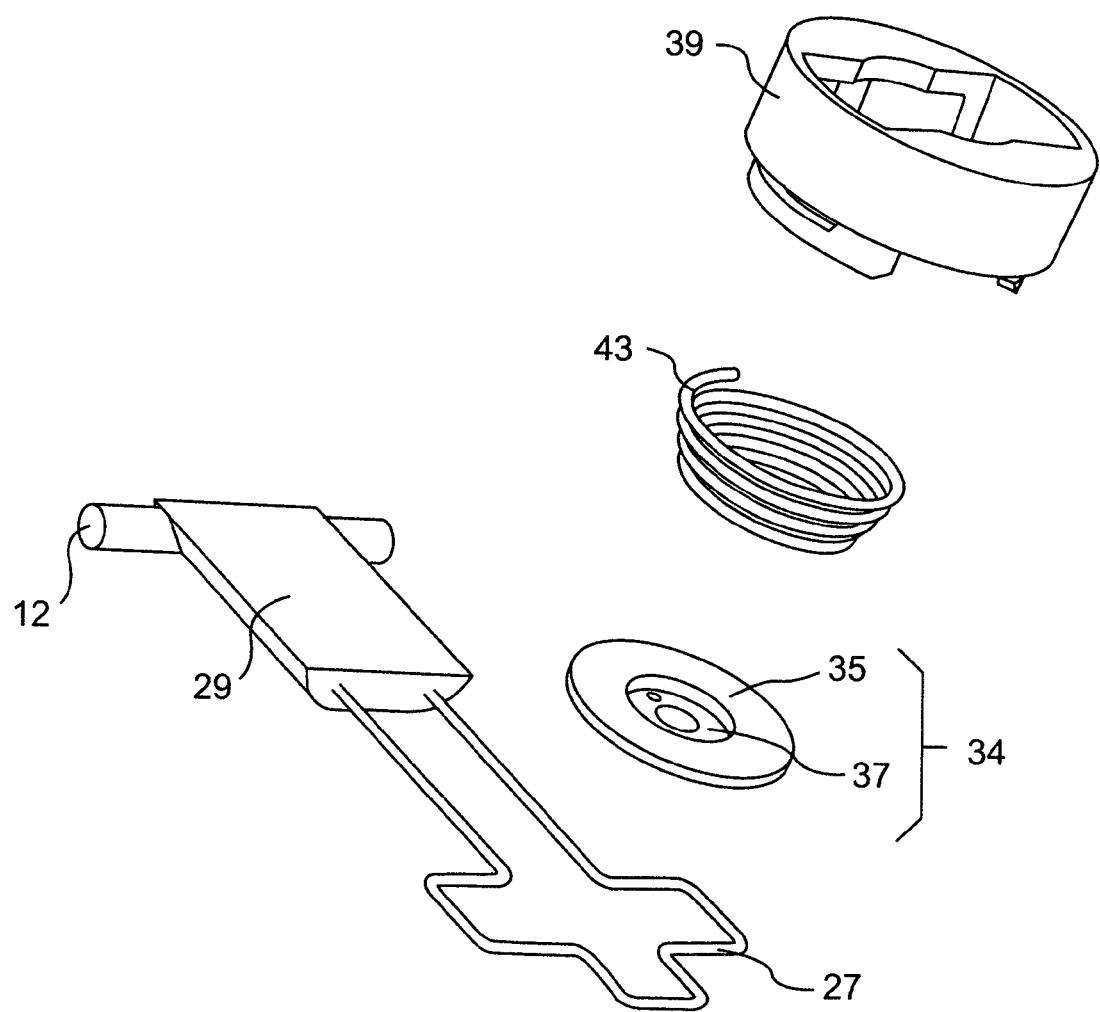

As shown in FIGS. 2, 8A and 8B, the housing 39 may contain a spring 43 whereby the atomizer assembly 34 is held in the housing 39 in a manner that allows it to move up and down under the bias of the spring 43. This arrangement accommodates variations in the heights of the wicks 56 of different reservoir assemblies 30, thereby reducing the need for dimensional precision in the design of the reservoir assembly 30 and the wick 56. The spring 43 preferably has a very small spring coefficient so that variations in the height of the wicks 56 do not significantly affect the amount of pressure a wick 56 exerts on the atomizer assembly 34. This assures that the atomizing performance is maintained irrespective of variations in the height of the wick 56. It will be appreciated that other resilient elements may be used in place of the spring 43 to allow for variation in the heights of the wicks 56, so long as such other resilient elements do not significantly affect the amount of pressure the wick 56 exerts on the atomizer assembly 34.

More detailed descriptions of the wire-like support 27 for supporting the atomizer assembly 34, the housing 39 and the spring 43 are given in U.S. Pat. No. 6,843,430, noted above, and in copending U.S. patent application Ser. No. 10/304,215 (now published as U.S. Patent Application Publication No. 2004/0108390 A1), filed Nov. 26, 2002, which is assigned to the assignee of this invention and incorporated herein by reference. These applications disclose, inter alia, a variety of wire-like supports 27 for supporting the atomizer assembly 34, which may be applied to the present invention by one of ordinary skill in the art.

Figure 6:
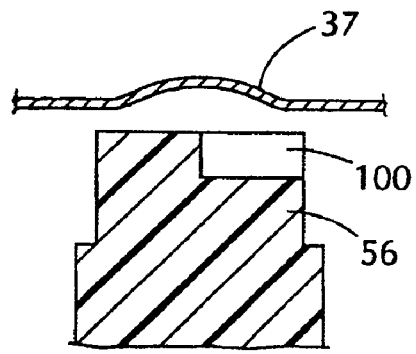
FIGS. 6 and 7 are enlarged elevational views showing the upper end of the wick in cross-section as it is being placed in an engagement position and after it is in the engagement position, respectively.
Figure 5:
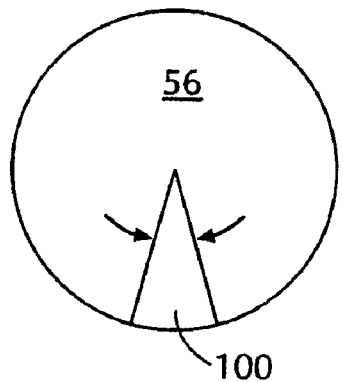
FIG. 5 is a top view of the upper end of the wick of FIG. 3.

As shown in FIGS. 8A and 8B, the atomizer assembly 34 comprises an annularly shaped piezoelectric actuator element 35 and a circular orifice plate 37, which extends across and is soldered or otherwise affixed to the actuator element 35. A construction of a piezoelectrically actuated vibrator type atomizer assembly is per se well known and is described, for example, in U.S. Pat. No. 6,296,196, which is incorporated herein by reference. Accordingly, the atomizer assembly 34 will not be described in detail except to say that when alternating voltages are applied to the opposite upper and lower sides of the actuator element 35, these voltages produce electrical fields across the actuator element and cause it to expand and contract in radial directions. This expansion and contraction is communicated to the orifice plate 37, causing the orifice plate 37 to flex so that a center region thereof vibrates up and down. The center region of the orifice plate 37 is domed slightly upward (see FIGS. 2, 6 and 7) to provide stiffness and to enhance atomization. The center region is also formed with a plurality of minute orifices (not shown) that extend through the orifice plate 37 from the lower or under surface of the orifice plate 37 to its upper surface. A flange (see FIGS. 6 and 7) is provided around the central domed region.

In operation, the batteries 26 supply electrical power to circuits on the printed circuit board 28 and these circuits convert this power to high frequency alternating voltages. A suitable circuit for producing these voltages is shown and described in U.S. Pat. No. 6,296,196, noted above. As described in that patent, the device may be operated during successive on and off times. The relative durations of these on and off times can be adjusted by an external switch actuator (fragrance adjustment lever) 40 (see FIG. 9) located on the outside of the housing 22 and coupled to a switch element (not illustrated) on the printed circuit board 28.

Figure 7:
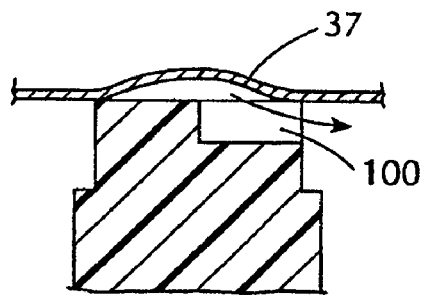

When the atomizer assembly 34 is in a state of engagement with a reservoir assembly 30, the flange of the orifice plate 37 is positioned to be in contact with (or in close proximity to) the upper end of the wick 56, as shown in FIGS. 2 and 7. Although not shown in the figures, the apparatus 20 may be designed so that the upper end of the wick 56 additionally or alternatively contacts the actuator element 35. The wick 56 delivers liquid from within the liquid container 31 by capillary action to the underside of the orifice plate 37 which, upon vibration, causes the liquid to pass through its orifices and to be ejected from its opposite side (i.e., the upper surface) in the form of very small droplets. The atomized liquid exits the apparatus 20 through the exit port 41.

Because of manufacturing tolerances, dimensional variations may occur, for example, in the wicks 56 of different reservoir assemblies 30. Since it is part of the intended operation of the apparatus 20 that, over time, a user will rotate the cartridge 60 so that different reservoir assemblies 30 will be successively engaged with the atomizer assembly 34 so as to have different fragrances dispensed, and since the cartridge 60 itself will need to be replaced upon consumption of the liquid in the liquid containers 31, it is desirable that performance be kept at a substantially constant level even as different reservoir assemblies 30 are successively used. In that regard, such a constant level of performance may be obtained because the atomizer assembly 34 is resiliently mounted, so that the upper end of a wick 56 will always press against the under surface of the orifice plate 37 and/or the actuator element 35 irrespective of dimensional variations which may occur due to manufacturing tolerances. That is, if the wick 56 of a newly engaged reservoir assembly 30 is higher or lower than the wick 56 of the previously engaged reservoir assembly 30, the action of the spring 43 will allow the atomizer assembly 34 to move up or down as required according to the elevation of the wick 56 in the newly engaged reservoir assembly 30. Thus, each subsequently engaged wick 56 will properly press against the underside of the orifice plate 37 and/or the actuator element 35.

The wick 56 is preferably of a solid, dimensionally stable material, such as a solid, porous plastic material, so that it will not become deformed when pressed against the underside of the resiliently supported orifice plate 37. Examples of such solid, dimensionally stable wicks 56 are described in copending U.S. patent application Ser. No. 10/412,911 (now published as U.S. Patent Application Publication No. 2004/0200907 A1), filed on Apr. 14, 2003, which is assigned to the assignee of this invention and incorporated herein by reference. In a preferred embodiment a solid, porous plastic material sold by MicroPore Plastics, Inc. of Stone Mountain, Ga., or the Porex Corporation of Fairburn, Ga., is employed. This plastic material is preferably high molecular weight polyethylene, although other materials may be suitable. A more detailed discussion of wicks as they pertain to this invention may be found in U.S. patent application Ser. No. 10/412,911 (U.S. Patent Application Publication No. 2004/0200907 A1), noted above.

Another concern pertaining to the use of, or switching between, multiple reservoir assemblies 30 is that the flow of liquid to the atomizer assembly 34 not be delayed upon engagement of a new reservoir assembly 30 therewith. To ensure instantaneous flow in this situation, the apparatus may employ a wick 56 having a top surface that has different levels, such that a portion 100 of the wick 56 is not in contact with the orifice plate 37 or the actuator element 35, as shown in FIGS. 2-7. (As discussed above, in a state of engagement with the atomizer assembly 34, the upper end of the wick 56 is generally substantially in contact with the flange portion on the periphery of the domed portion of the orifice plate 37, and the wick 56 may also be in contact with the actuator element 35.) The non-contact portion 100 provides unobstructed passage to the atmosphere when the reservoir assembly 30 is engaged with the atomizer assembly 34, as shown in FIG. 7. A detailed description of this wick, as well as of a number of variations thereof applicable to this invention, is found in copending U.S. patent application Ser. No. 10/412,911 (U.S. Patent Application Publication No. 2004/0200907 A1), noted above. As explained in that application, wicks 56 having a configuration such as that described above have been shown to consistently provide instantaneous flow of liquid upon engagement of a reservoir assembly 30 with the atomizer assembly 34. While such a configuration of wick 56 is preferable, it is not required for this invention.

Figure 11:
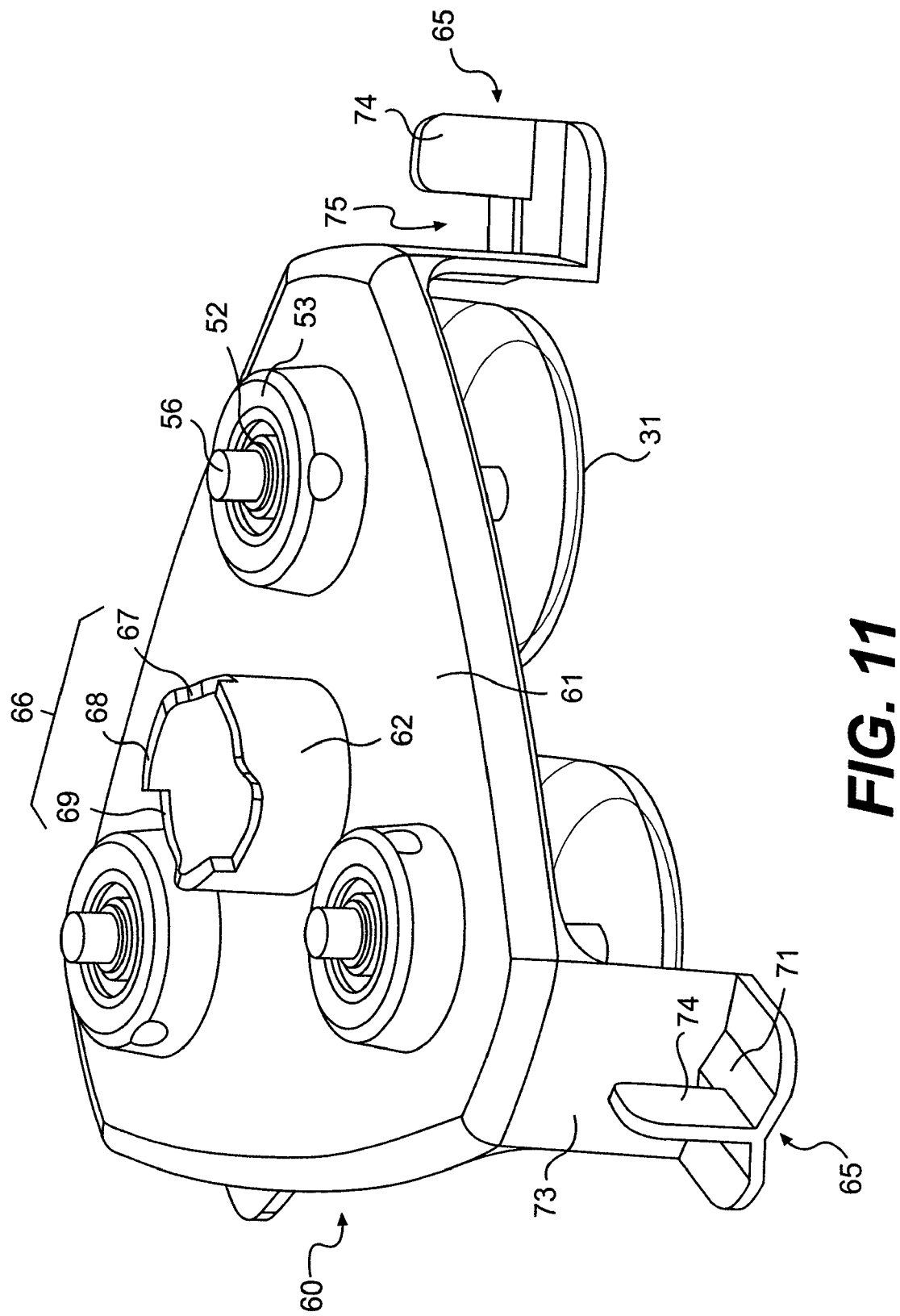
FIG. 11 is a perspective view of the cartridge of the atomization apparatus of FIG. 1.

The installation and removal of the cartridge 60, and the structures pertaining thereto, will be explained with reference to FIGS. 1, 10-14 and 22-24. The cartridge 60 is removably secured in the housing 22 by means of cartridge retention snaps 70, which are formed to be stiff but resilient, e.g., made of a hard plastic material. The cartridge retention snaps 70 are extensions of the cylindrical portion 14 (see FIGS. 22-24) of the housing 22, preferably formed integrally with the cylindrical portion 14. As shown in FIGS. 1, 10, 12-14 and 22-24, the two snaps 70 are themselves semi-cylindrical portions, which together form an effectively cylindrical portion. This effectively cylindrical portion has an outer circumference that is just smaller than the inner circumference of a cut-away tubular portion 62, which is formed in the center of the cartridge 60 to extend vertically therethrough, as shown in FIG. 11. Thus, the snaps 70 fit snugly in the tubular portion 62, as shown in FIGS. 1 and 12-14. As explained presently, the snaps 70 permit the cartridge 60 to be locked in the housing 22 while allowing the cartridge 60 to rotate.

To install the cartridge 60 into the housing 22, the free ends of the snaps 70 are squeezed together and inserted into the tubular portion 62 of the cartridge 60. Each of the snaps 70 has at its free end a flanged portion 63 including a flange 64. When the free ends of the snaps 70 are inserted through the tubular portion 62 of the cartridge 60 to a sufficient extent that the flanges 64 clear the bottom of the tubular portion 62, the restorative force of the snaps 70 will cause the flanged portions 63 of the snaps 70 to move away from each other toward their pre-insertion (unsqueezed together) positions, thus locking the cartridge 60 into the snaps 70 and thence into the housing 22, by means of the flanges 64. In this secured or locked position, shown in FIGS. 1 and 12-14, as stated, the effectively cylindrical portion constituted by the snaps 70 fits snugly in the tubular portion 62 of the cartridge 60, permitting the cartridge 60 to rotate about the snaps 70.

To remove the cartridge 60 from the housing 22, the free ends of the snaps 70 are squeezed together to the extent that the flanges 64 clear the inner walls of the tubular portion 62 of the cartridge 60, so that the snaps 70 can be slid back out of the tubular portion 62, hence out of the cartridge 60. Thus, the cartridge 60 and snaps 70 are formed to permit quick, easy and convenient insertion of a cartridge 60 into, and removal from, the housing 22, and to provide secure installation of the cartridge 60 in the housing 22 with smooth and easy rotation of the cartridge 60 while installed therein.

As an alternative to the snaps 70, any other appropriate securing means that permits removable but secure retention of the cartridge 60 in the housing 22, and allows the cartridge 60 to rotate while in the secured state, such as may be contemplated by one of ordinary skill in the art, may be employed.

The operations and structures pertaining to engaging and disengaging individual reservoir assemblies 30 and switching between reservoir assemblies 30 will be explained with reference to FIGS. 1, 9 and 11-14. The cartridge 60 is designed to rotate such that any one of a plurality of reservoir assemblies 30 can be engaged with the atomizer assembly 34 in order that any one of a variety of volatile, e.g., fragrant, substances contained in the respective liquid containers 31 can be successively dispensed. Rotation of the cartridge 60 (to be explained more fully below) may be performed manually by grasping the housing 22 and the handles (manual rotation levers) 65 and sliding the handles 65 relative to the housing 22. As will become clear presently, the configuration illustrated in the drawings is one in which the cartridge 60 is rotatable in the clockwise direction with respect to the handles 65. However, an alternative configuration in which the cartridge 60 is rotatable in the counterclockwise direction is also possible.

The apparatus is provided with a cam feature that causes the atomizer assembly 34 to alternately engage and disengage from successive reservoir assemblies 30 as the cartridge 60 is rotated. The cam feature also keeps the atomizer assembly 34 out of the path of motion of reservoir assemblies 30 as they are being rotated, which prevents damage to the atomizer assembly 34 and the wicks 56 and ensures proper engagement, as discussed below. The cam feature is constituted by a circumferential cross-sectional surface 66 on the upper end of the tubular portion 62 of the cartridge 60, shown in FIG. 11. As shown in that figure, the upper circumferential cross-sectional surface 66 is formed to alternately rise and fall in the direction of travel around the circumference. Specifically, the upper circumferential cross-sectional surface 66 follows a pattern consisting of a gradual ascent 67 to a plateau 68 (flat portion of highest elevation) followed by a sudden drop to a valley portion 69 (flat portion of lowest elevation). This pattern is repeated three times along the circumference.

This alternating rising and falling upper circumferential cross-sectional surface 66 of the tubular portion 62 of the cartridge 60 operates in conjunction with the pivot arm 29 which, as shown in FIGS. 1 and 12-14, rests on the upper circumferential cross-sectional surface 66. As discussed above, the pivot arm 29 is connected at one end (pivot point 29a) to the axle 12 and at the other end to the wire-like support 27, which in turn is connected at its other end to the atomizer assembly 34. Pivoting the pivot arm 29 by rotating the axle 12 about the pivot point 29a causes the wire-like support 27, and thence the atomizer assembly 34, to move up and down. As the cartridge 60 is rotated, the pivot arm 29 rides upon the upper circumferential cross-sectional surface 66, successively rising and falling, following the topography of the upper circumferential cross-sectional surface 66. Thus, as the cartridge 60 is rotated, the atomizer assembly 34 connected to the pivot arm 29 also successively rises and falls according to the contour of the upper circumferential cross-sectional surface 66, in conjunction with the pivot arm 29.

Figure 12:
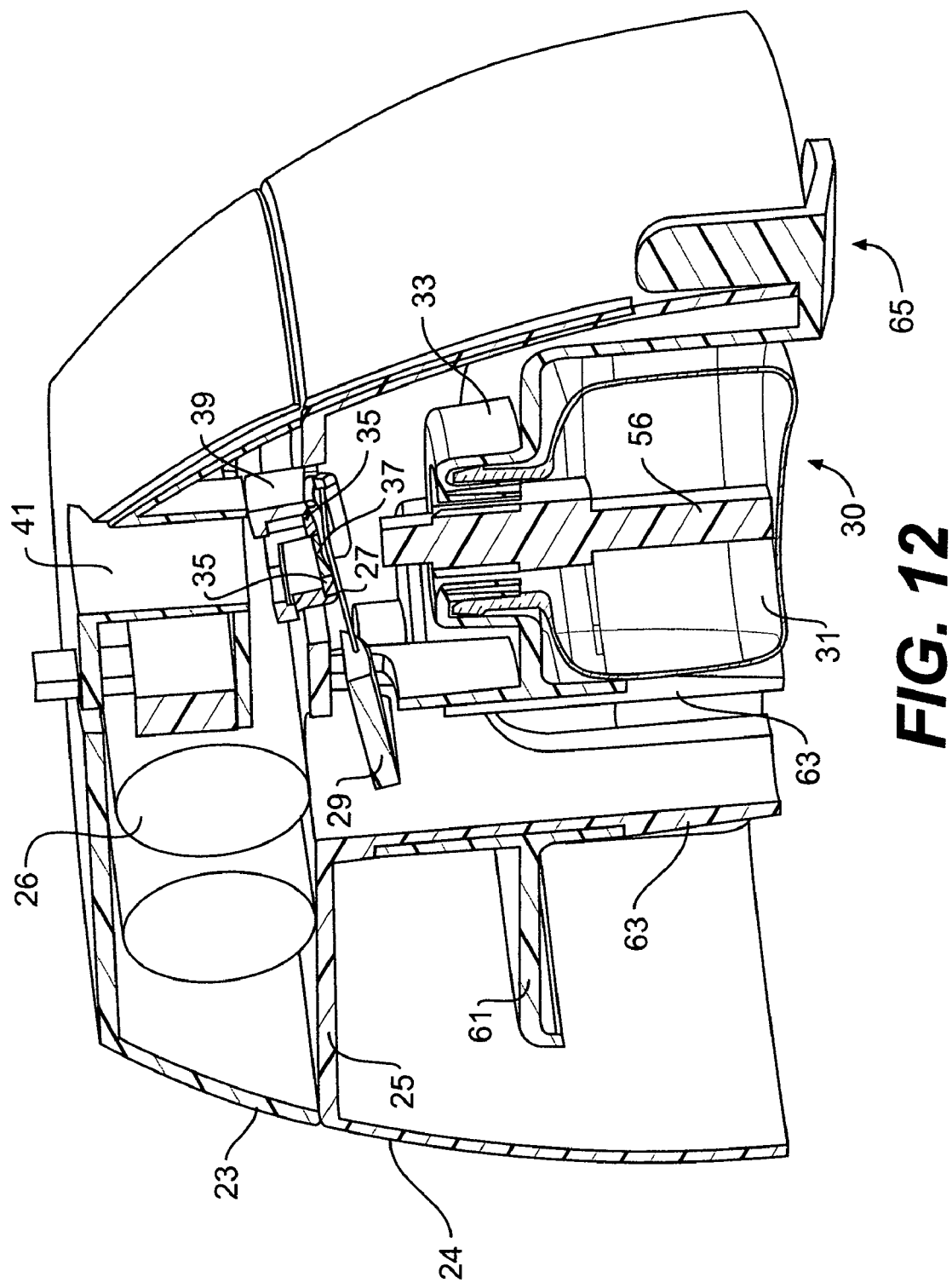
FIG. 12 is a cut-away perspective view of the atomization apparatus of FIG. 1 showing a state in which the atomizer assembly is disengaged from a reservoir assembly.
Figure 13:
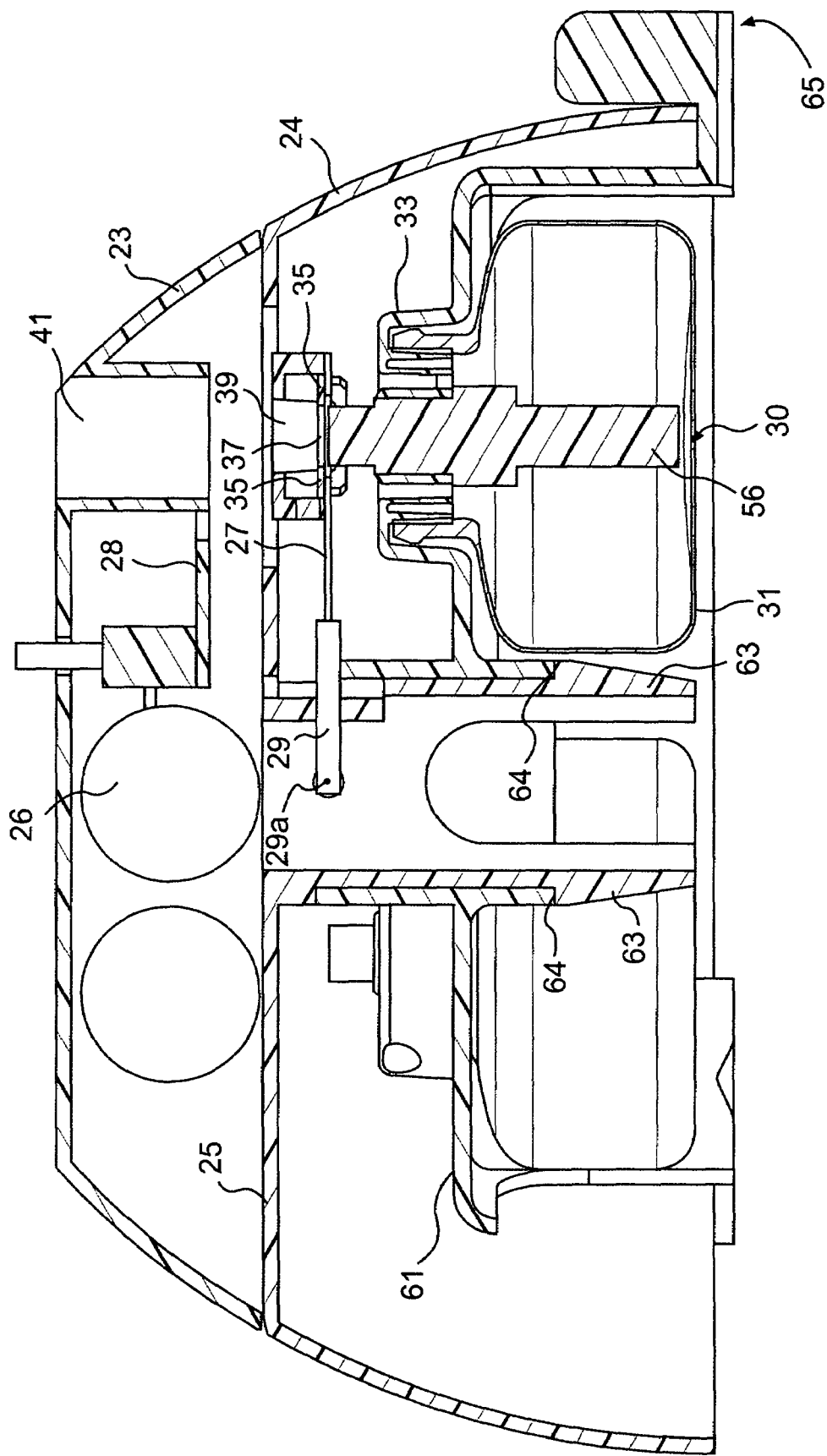
FIG. 13 is a cross-sectional, elevational view of the atomization apparatus of FIG. 1 showing a state in which the atomizer assembly is engaged with a reservoir assembly.
Figure 14:
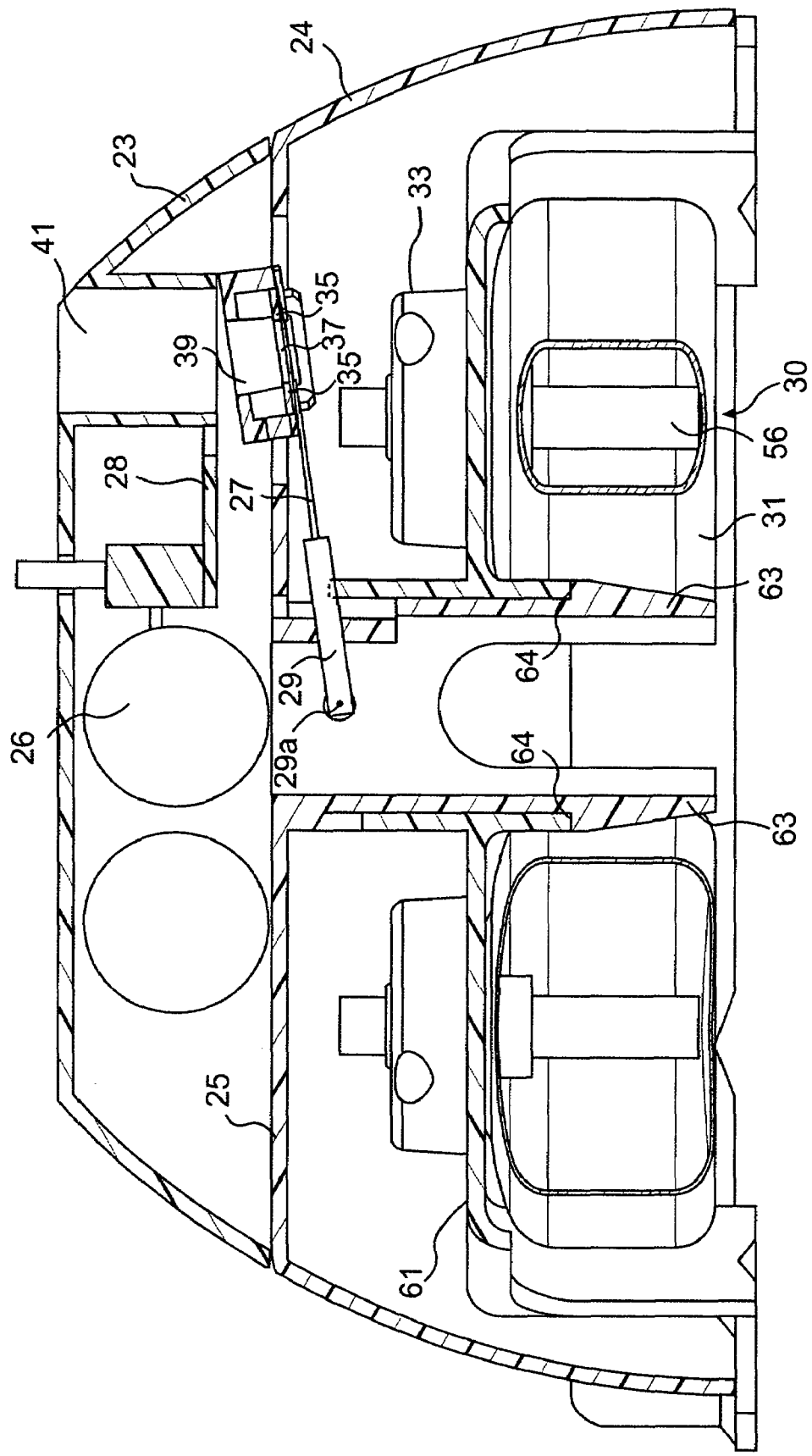
FIG. 14 is a cross-sectional, elevational view of the atomization apparatus of FIG. 1 showing a state in which the atomizer assembly is disengaged from a reservoir assembly.

As stated above, when the cartridge 60 is rotated, the atomizer assembly 34 alternately engages with and disengages from a successive reservoir assembly 30. That is, when a reservoir assembly 30 is brought into alignment with the atomizer assembly 34, the atomizer assembly 34 is caused to be engaged with the reservoir assembly 30. (FIGS. 1 and 13 show this state of engagement.) When the reservoir assembly 30 is moved out of alignment with the atomizer assembly 34, the atomizer assembly 34 is disengaged therefrom. (FIGS. 12 and 14 show this state of disengagement.) More specifically, as shown in FIG. 11, the topography of the upper circumferential cross-sectional surface 66 is configured so that the beginning of each valley portion 69 (that is, just after the drop) is located at a position along the circumference that is closest to the center of a plug 33 of a reservoir assembly 30, while each pair of gradual ascent 67 and subsequent plateau 68 is located at a position along the circumference that is closest to a portion of the platform 61 (of the cartridge 60) situated in between the centers of two plugs 33. Thus, each time the pivot arm 29 and atomizer assembly 34 drop to their lowermost position, in the valley portion 69, they are located at a position along the circumference of the tubular portion 62 that is in alignment (i.e., for the purpose of engagement) with one of the reservoir assemblies 30. At this time, when the atomizer assembly 34 drops into this lowest position, it engages with the wick 56 of the liquid container 31 with which it is aligned.

The position in which the atomizer assembly 34 is engaged with a reservoir assembly 30 (FIGS. 1 and 13) may be referred to as an engagement position. The term "engagement position" may be applied not only to the atomizer assembly 34 and the reservoir assembly 30 (and any parts thereof, such as the liquid container 31 and the wick 56), but also to the cartridge 60 and to the entire apparatus. (For the sake of convenience, the discussion herein refers to engagement of the atomizer assembly 34 variously with the reservoir assembly 30, the liquid container 31, and the wick 56. This usage is not to be taken to contradict other accounts of the details of the engagement (e.g., concerning which part(s) of the atomizer assembly 34 engage with which part(s) of the reservoir assembly 30), such as are given herein or in other documents referred to herein and/or incorporated herein by reference.)

When the cartridge 60 is an engagement position and is subsequently rotated, the engaged reservoir assembly 30, including the liquid container 31 and, in particular, the wick 56, is first rotated away from the atomizer assembly 34, hence disengaging therefrom. Then, the atomizer assembly 34 begins its gradual ascent upward along the upper circumferential cross-sectional surface 66 of the tubular portion 62, thus moving to a position above the level of the wicks 56. As the upper circumferential cross-sectional sectional surface 66 rotates under the pivot arm 29, the atomizer assembly 34 continues to rise, reaching its highest position when the plateau 68 of the upper circumferential cross-sectional surface 66 has been rotated so as to be under the pivot arm 29. The atomizer assembly 34 remains disengaged until the plateau 68 passes the pivot arm 29 and the pivot arm 29 and atomizer assembly 34 drop down to their lowest position, with the pivot arm 29 resting in the valley portion 69 of the upper circumferential cross-sectional surface 66. As discussed above, at this time, when the atomizer assembly 34 drops down, it is in alignment with the next reservoir assembly 30 and engages the wick 56 thereof.

Thus, engagement of the atomizer assembly 34 with a wick 56 occurs with the drop-down of the atomizer assembly 34 onto the wick 56, while disengagement of the atomizer assembly 34 from the wick 56 occurs when the wick 56 is rotated away from the atomizer assembly 34. The elevation of the atomizer assembly 34 above the level of the wicks 56 that occurs after disengagement provides for a smooth reengagement process and prevents damage to the atomizer assembly 34 and the next wick 56 to be engaged. Specifically, the short vertical distance constituting the drop-down and the relative weights of, on the one hand, the pivot arm 29, the wire-like support 27, and the atomizer assembly 34, and, on the other hand, the wick 56 and the other components of the reservoir assembly 30, are such as to provide for a gentle and smooth engagement. Moreover, the vertical drop-down distance, albeit short, prevents a possible collision, misalignment or non-alignment between a next-to-be-engaged wick 56 and the atomizer assembly 34. If, after disengagement, the atomizer assembly 34 remained at the level of the disengaged wick 56, and the top of the subsequent wick 56 extended higher or lower than the top of the disengaged wick 56, such a collision, misalignment or non-alignment could occur. As discussed above, manufacturing tolerances are such that different wicks 56 may be made having different heights.

Thus, by virtue of the cam feature, namely, the upper circumferential cross-sectional surface 66 of the tubular portion 62 of the cartridge 60, operating in tandem with the pivot arm 29, the rotation of the cartridge 60 is conjoined with the engagement/disengagement of the reservoir assemblies 30. That is, on account of the cam structure or contour of the upper circumferential cross-sectional surface 66, the rotation of the cartridge causes the atomizer assembly 34 to engage with a reservoir assembly 30 when that reservoir assembly 30 is brought into alignment therewith and to disengage from a reservoir assembly 30 (with which it is engaged) when the atomizer assembly 34 moves out of alignment therewith.

The operation and structures pertaining to manual rotation of the cartridge 60 will be explained with reference to FIGS. 1 and 9-19. As stated above, the cartridge 60 may be rotated manually using the three handles (manual rotation levers) 65. The handles 65 are shaped and disposed in such a fashion as to be slidable (rotatable) around the perimeter of the housing 22 when the cartridge 60 is secured in the housing 22. As shown, for example, in FIGS. 1 and 9-11, the handles 65 may be formed as extensions of the cartridge 60. Specifically, the handles 65 may be formed, for example, as latches that extend from the bottom of each of the three legs 73 of the cartridge 60, radially outward and then upward, so as to form grips 74, disposed exterior to the housing 22, and so as to form slits 75, between the grips 74 and the legs 73 of the cartridge 60, through which the housing 22 slidably (rotatably) fits. The user grasps the grips 74 with one hand while holding the housing 22 with the other hand to rotate the cartridge 60 with respect to the housing 22.

As shown, for example, in FIGS. 9-11, 16 and 19, each handle 65 may be formed so as to have a convex portion 71 that fits into a corresponding concave portion 72 formed on the lower circumferential cross-sectional surface of the housing 22. The three concave portions 72 are equally spaced around the bottom circumference of the housing 22, and one of the concave portions 72 is aligned with the atomizer assembly 34 (see FIGS. 1 and 16; to be explained further below). The convex portions 71 are formed in alignment with the reservoir assemblies 30 (see FIG. 11) so that the concave portions 72 of the housing 22 come into alignment with and snap or click into place upon the convex portions 71 when the atomizer assembly 34 comes into alignment with and engages a reservoir assembly 30. Thus, when a user attempts to rotate the cartridge 60 from an engagement position (see FIG. 16), the convex portions 71 create a small resistance to rotation. A small amount of force from the user overcomes the resistance, causing the lower circumferential cross-sectional surface of the housing 22 to rise to the top of the convex portions 71 (see FIG. 19). When the housing 22 has been thus elevated, the cartridge 60 can freely rotate. When the cartridge 60 has been rotated to the position at which a given convex portion 71 reaches the next concave portion 72, the housing 22 falls back down as the three concave portions 72 fit and snap into place on the convex portions 71 (see FIG. 16).

Figure 9:
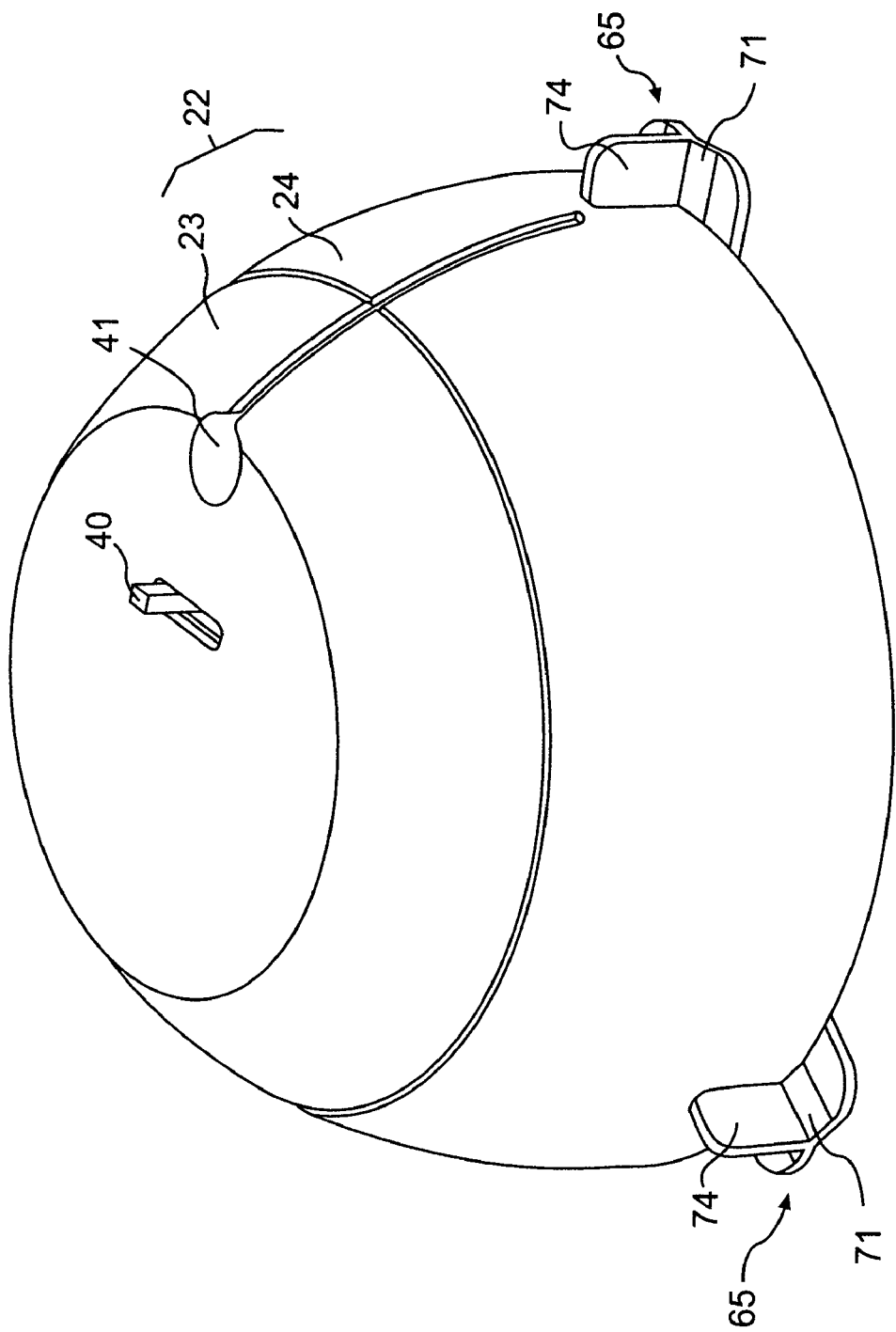
FIG. 9 is a perspective view of the atomization apparatus of FIG. 1 showing a state in which the apparatus is in an engagement position.
Figure 10:
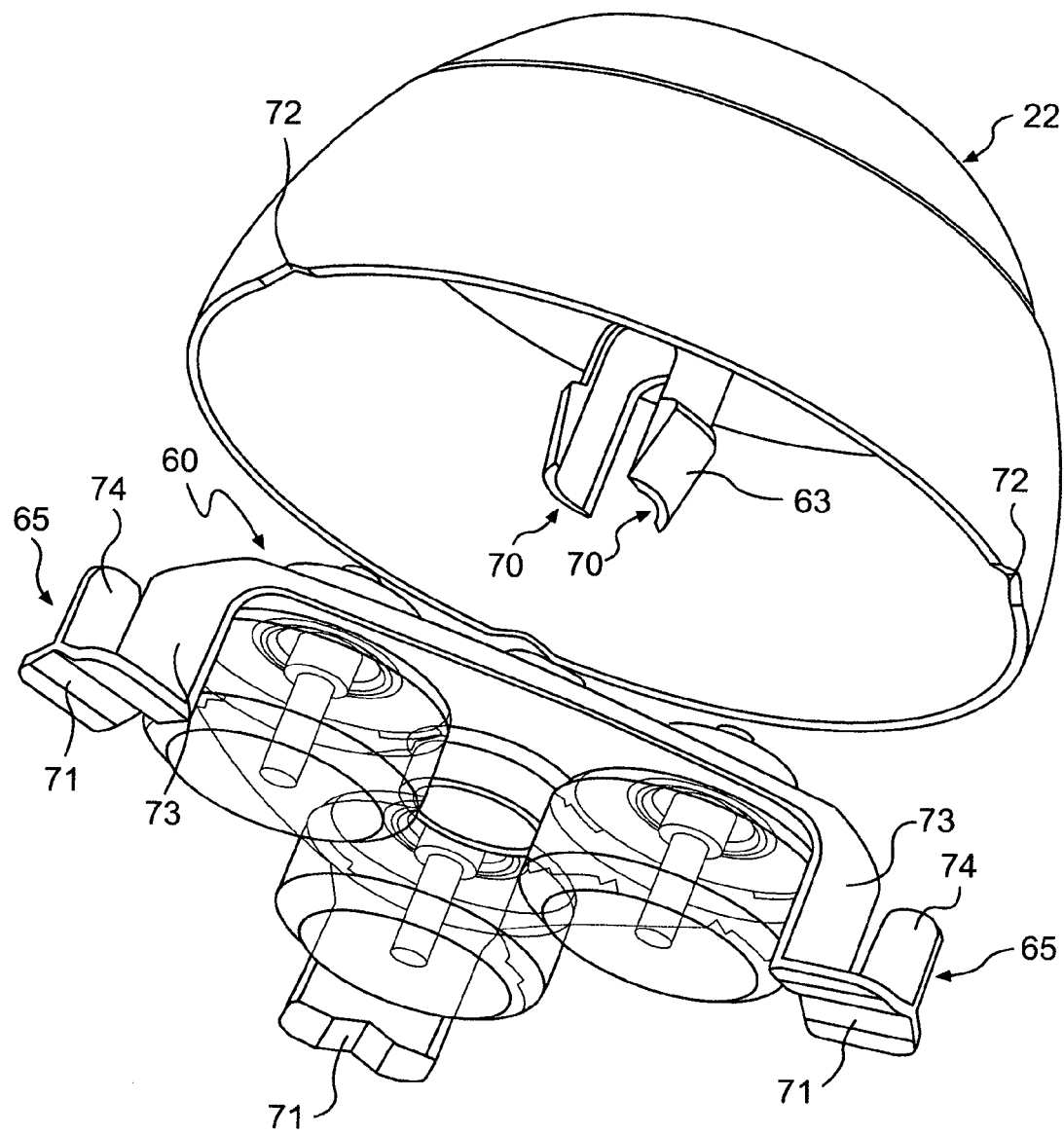
FIG. 10 is a perspective view showing the housing and the cartridge of the atomization apparatus of FIG. 1 in an unassembled state.
Figure 15:
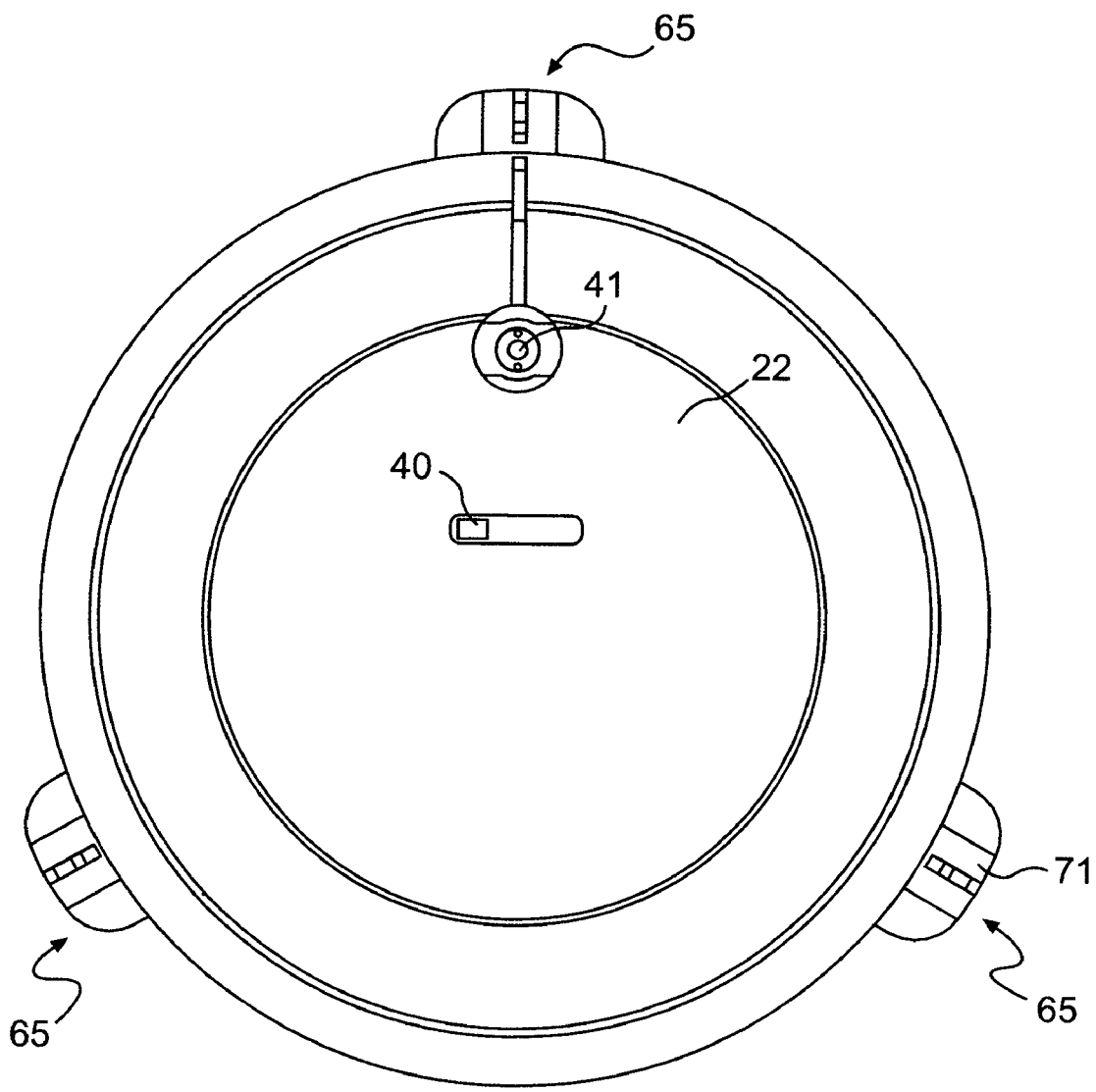
FIG. 15 is a top view of the atomization apparatus of FIG. 1 showing a state in which the apparatus is in an engagement position.
Figure 16:
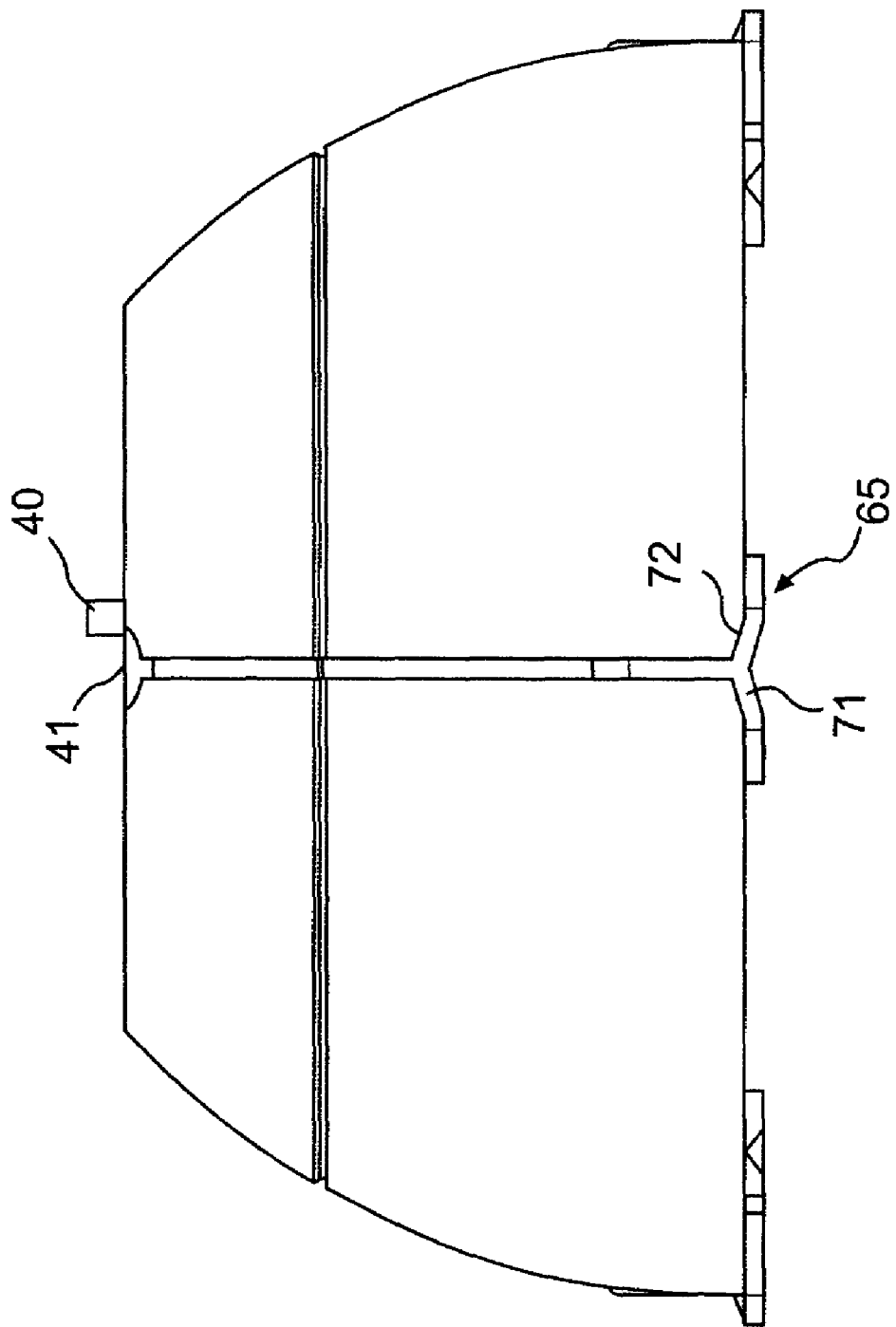
FIG. 16 is an elevational view of the atomization apparatus of FIG. 1 showing a state in which the apparatus is in an engagement position.
Figure 17:
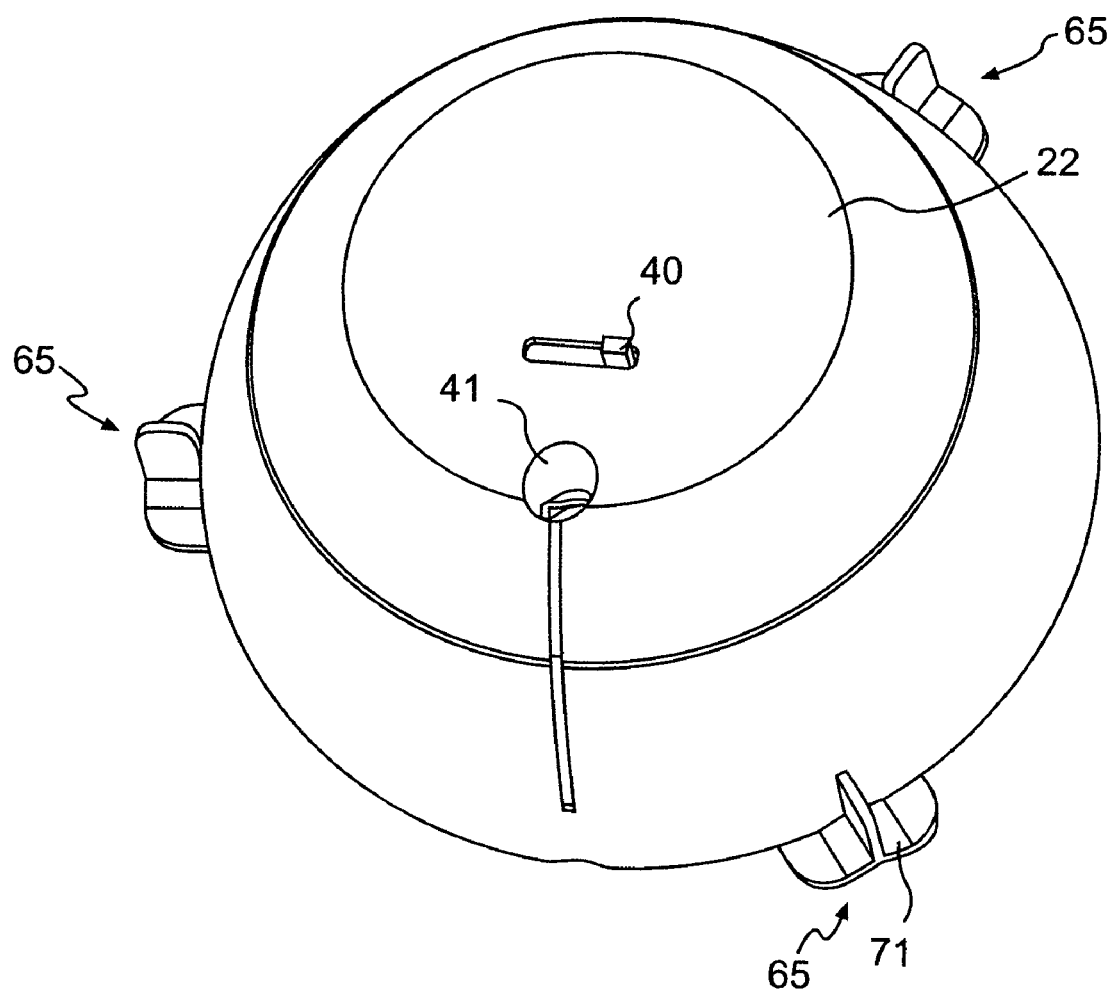
FIG. 17 is a perspective view of the atomization apparatus of FIG. 1 showing a state in which the apparatus is not in an engagement position.
Figure 18:
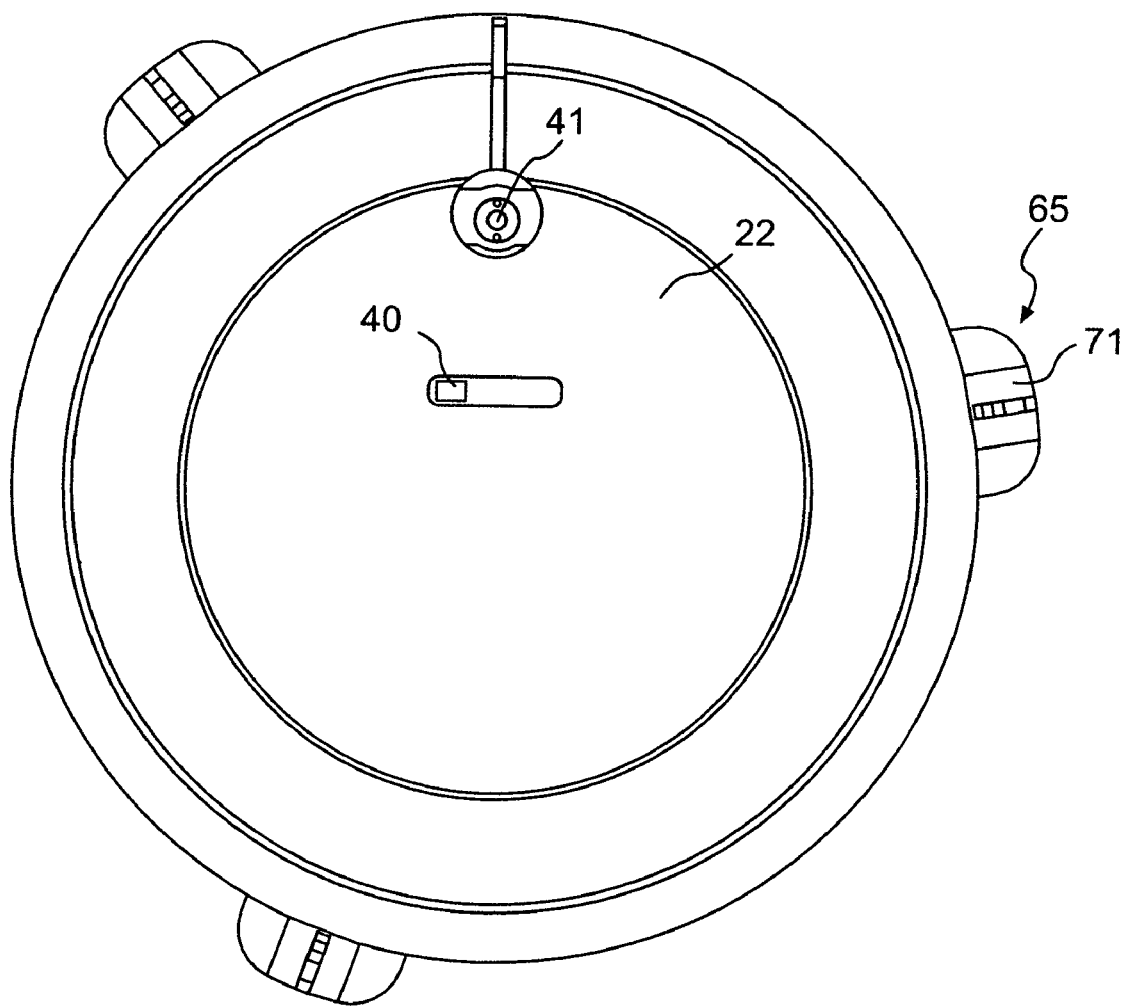
FIG. 18 is a top view of the atomization apparatus of FIG. 1 showing a state in which the apparatus is not in an engagement position.
Figure 19:
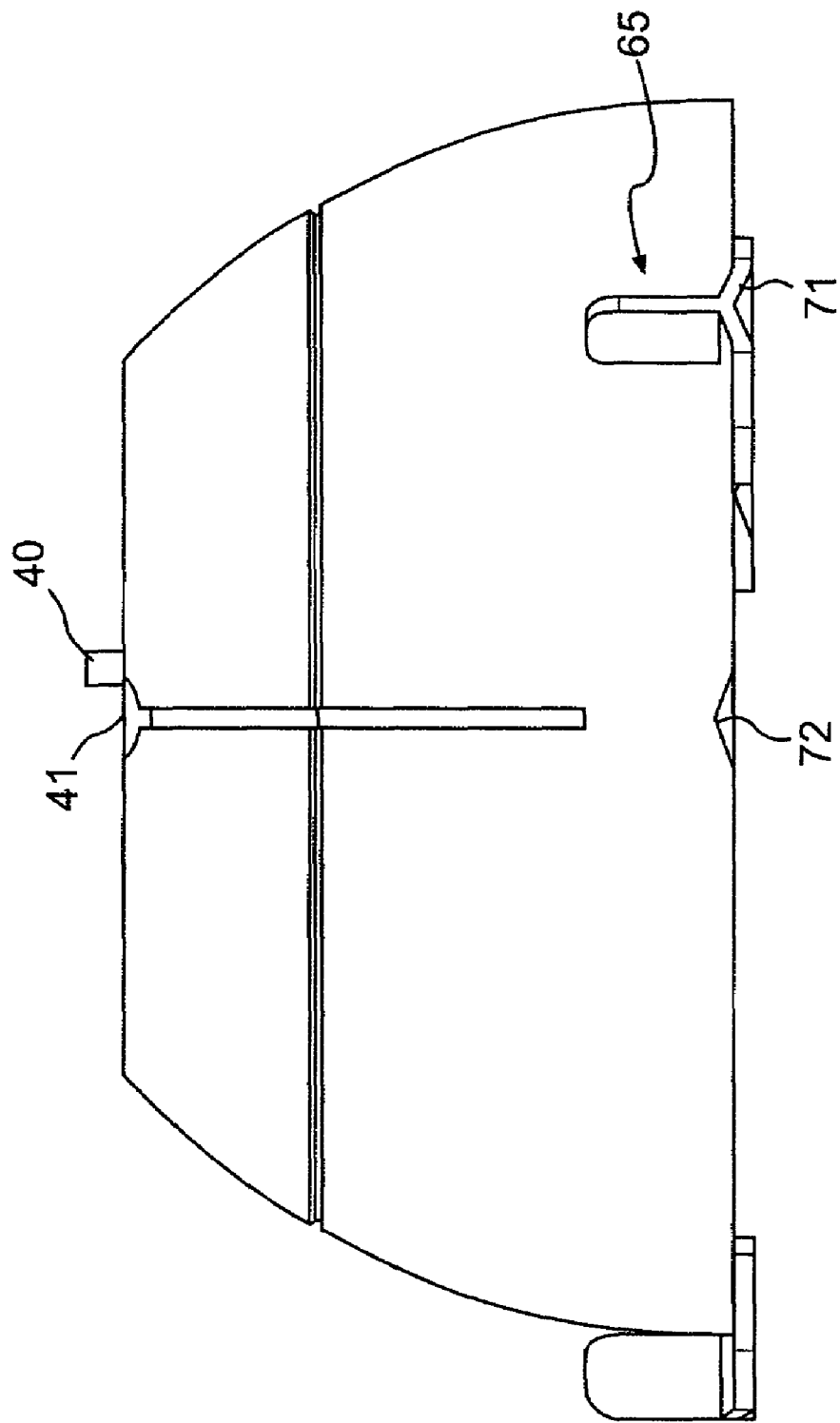
FIG. 19 is an elevational view of the atomization apparatus of FIG. 1 showing a state in which the apparatus is not in an engagement position.
Figure 20:
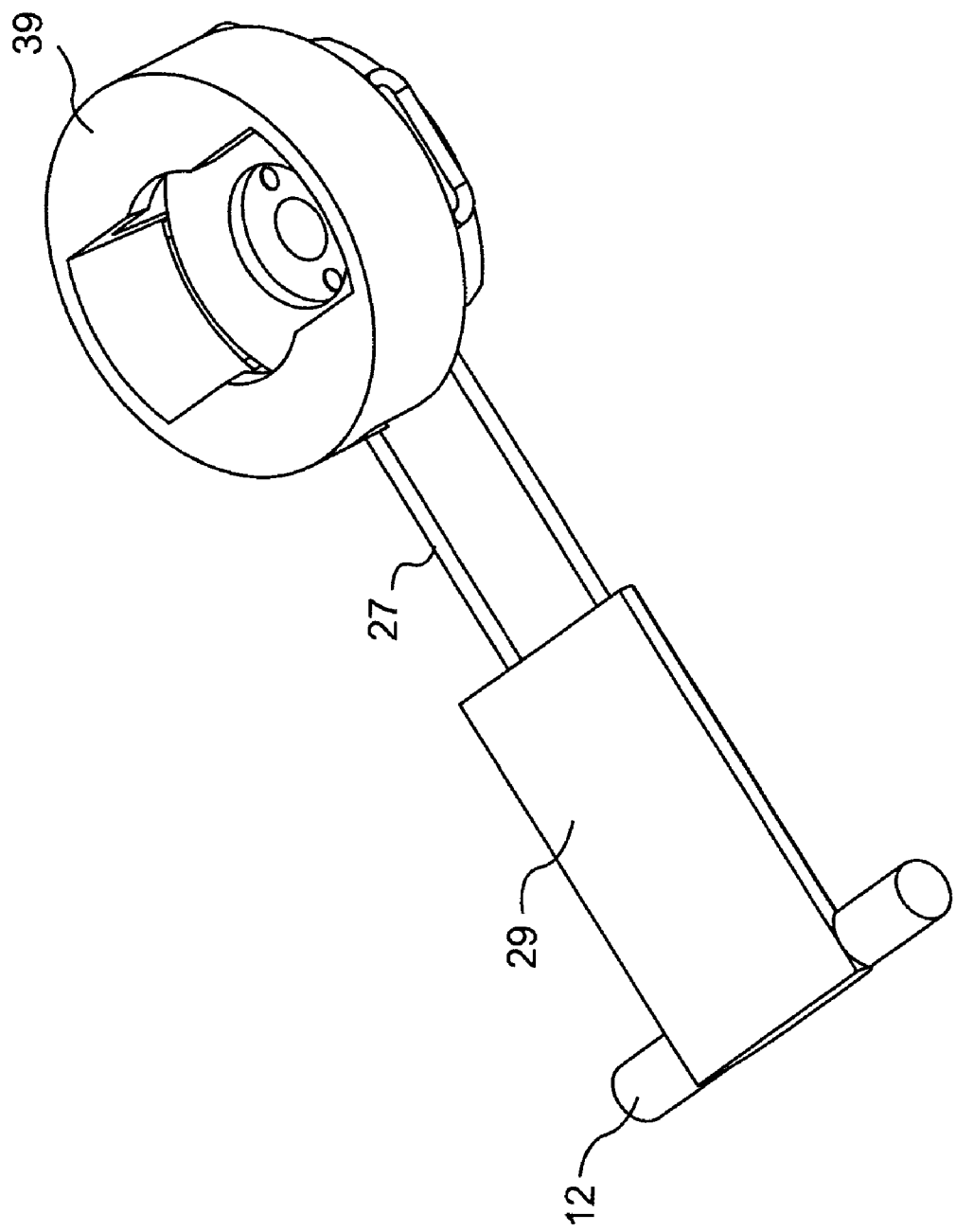
FIGS. 20 and 21 are perspective views of the pivot assembly supporting the atomizer assembly, as seen from above and from below, respectively.
Figure 21:
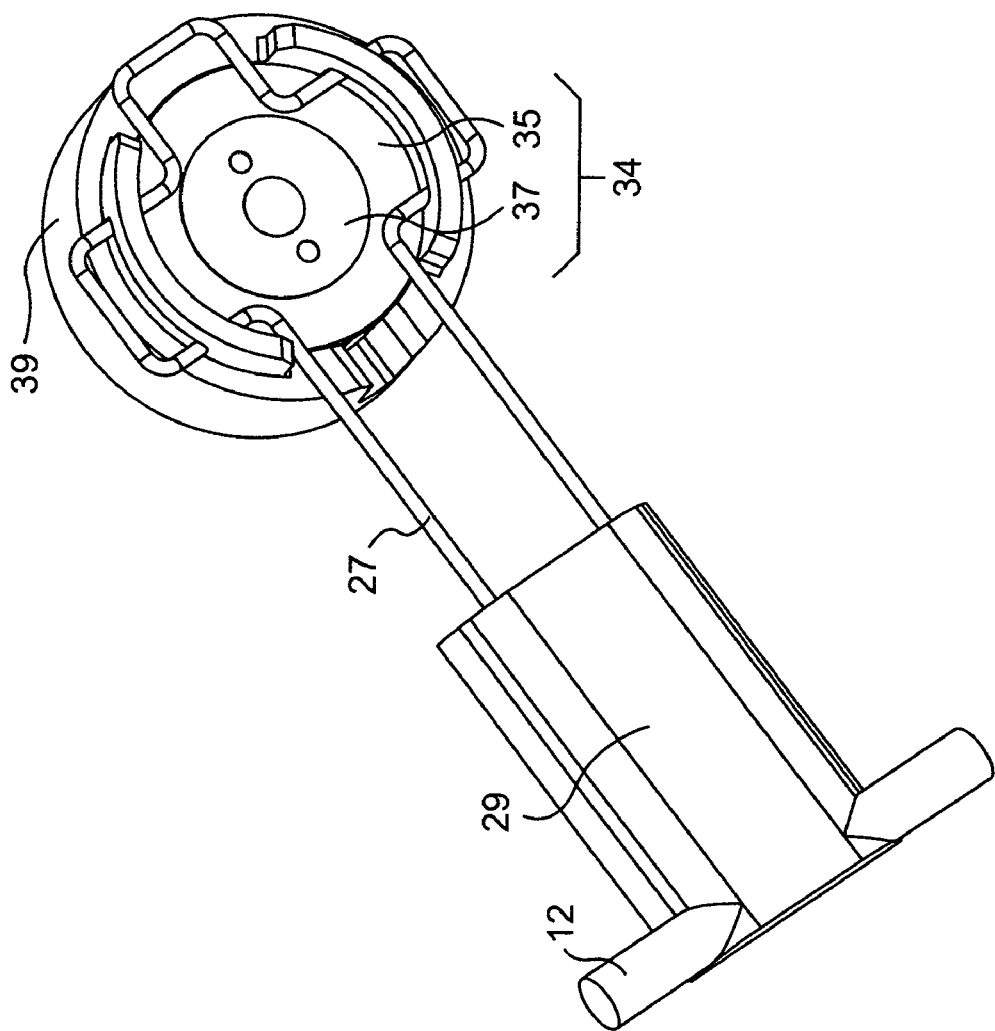
Figure 22:
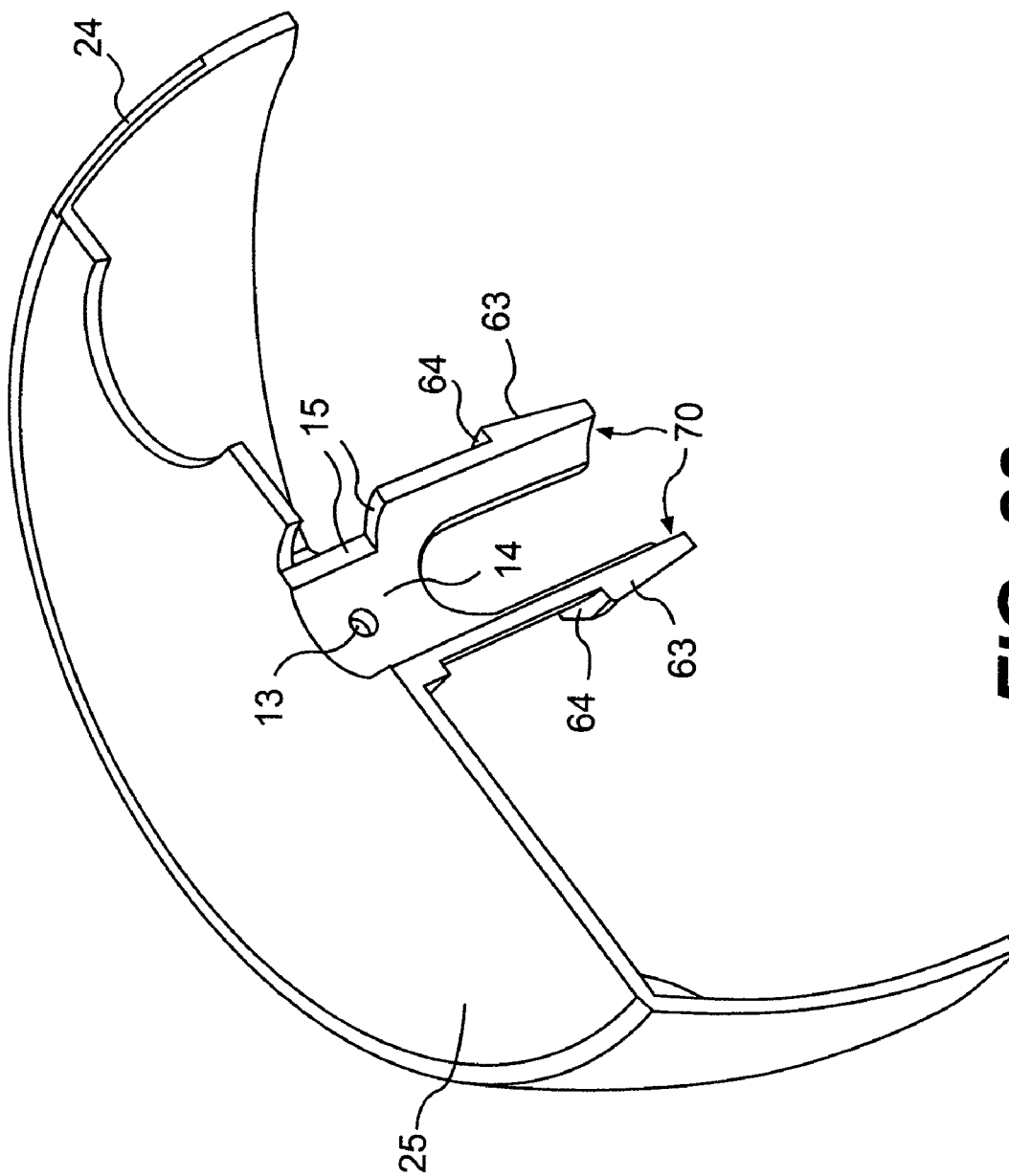
FIG. 22 is a cut-away perspective view of a portion of the housing of the atomization apparatus of FIG. 1.
Figure 23:
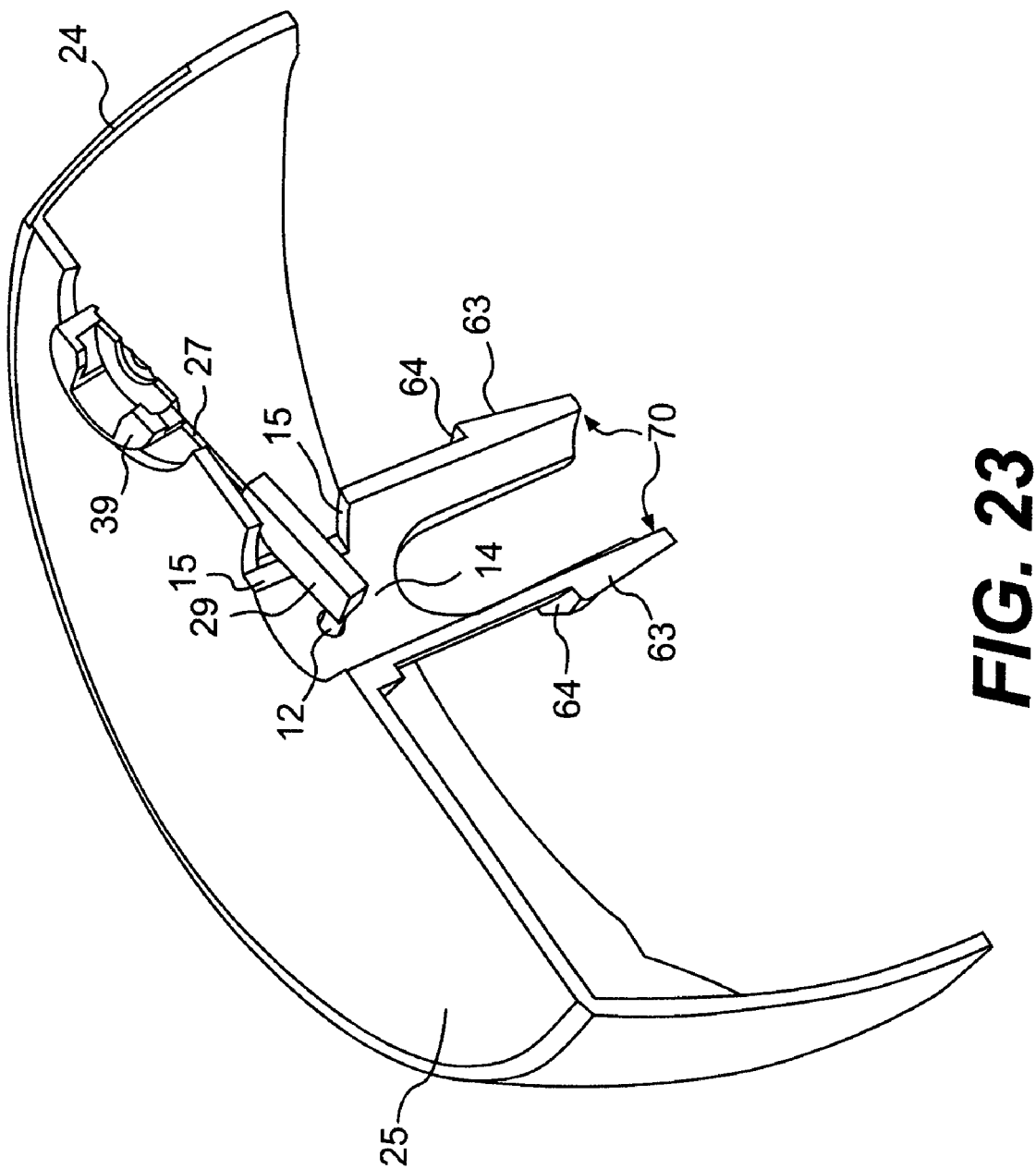
FIG. 23 is a cut-away perspective view showing a portion of the housing of the atomization apparatus of FIG. 1 and a portion of the pivot assembly supporting the atomizer assembly.
Figure 24:
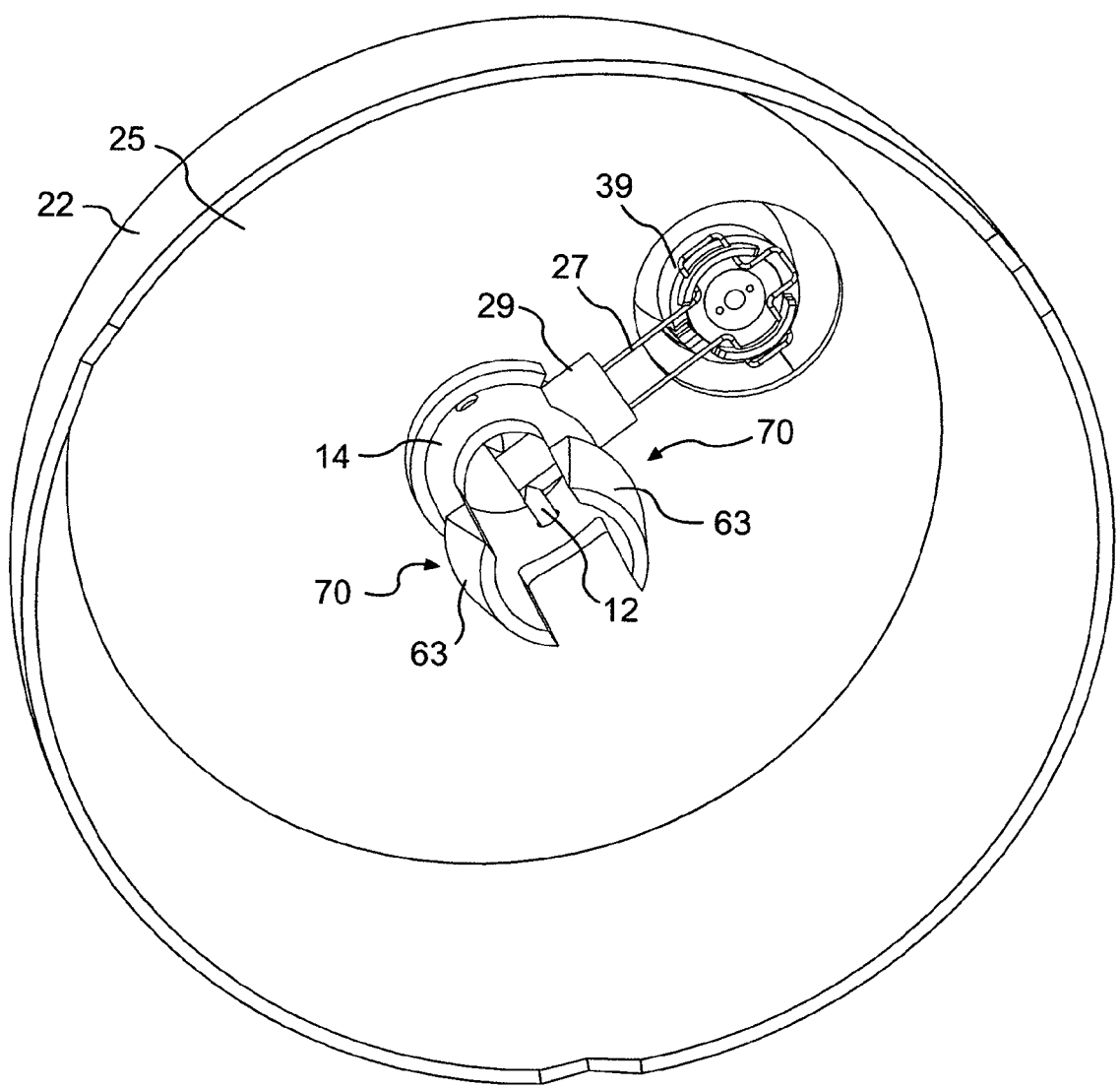
FIG. 24 is a perspective view of the housing of the atomization apparatus of FIG. 1, seen from below, showing the pivot assembly supporting the atomizer assembly.

Thus, the alignment and snapping into place of the concave portions 72 of the housing 22 with the handles 65, or convex portions 71, of the cartridge 60 serve as visual, auditory and tactile feedback to the user that the next reservoir assembly 30 has been brought into an engagement position. It will be appreciated that, since it will generally be expedient to dispose the exit port 41 and the fragrance adjustment lever (external switch actuator) 40 in alignment with the atomizer assembly 34 (and hence in alignment with one of the concave portions 72), the apparatus may easily be designed so that the exit port 41 and the fragrance adjustment lever 40 are brought into alignment with one of the handles 65 when the cartridge 60 is brought into an engagement position, thus providing further visual feedback to the user that the next reservoir assembly 30 has been brought into an engagement position. This is illustrated in FIGS. 9 and 15-19: FIGS. 9, 15 and 16 show the apparatus in an engagement position, in which the convex portions 71, the concave portions 72, the exit port 41 and the fragrance adjustment lever 40 are aligned; FIGS. 17-19 show the apparatus in a non-engagement position, in which, while the exit port 41 and the fragrance adjustment lever 40 (and hence the atomizer assembly 34) are aligned with one concave portion 72, the exit port 41, the fragrance adjustment lever 40, and the concave portions 72 are out of alignment with the convex portions 71.

While in the above-described embodiment cartridge 60 is configured to hold three reservoir assemblies 30, it will be appreciated that other embodiments of the invention are possible in which the cartridge 60 is configured to hold other numbers of reservoir assemblies 30. Such other configurations would take into account, for example, the number of plugs 33, handles 65, pairs of corresponding convex-concave portions, and repetitions of the rising-and-falling pattern of the upper circumferential cross-sectional surface 66 of the tubular portion 62 of the cartridge 60. In addition, while the above-described embodiment describes the reservoir assemblies 30 as being seated directly in the cartridge 60, it is also possible to seat the reservoir assemblies 30 in a magazine that is then mounted in the cartridge 60. Such a magazine might be desired, for example, to facilitate replacement of the reservoir assemblies 30, or for other design or manufacturing reasons.

The apparatus may also be designed so that the number of handles 65 is different from the number of reservoir assemblies 30. In that case, pairs of corresponding convex-concave portions may still be formed in one-to-one correspondence with the reservoir assemblies 30 in order to retain the above-discussed feedback feature. (The convex portions 71 could be formed as elements separate from, and not necessarily aligned with, the handles 65.) In addition, while the above-described embodiment shows the handles 65 formed entirely on the cartridge 60, other arrangements are possible (including modified construction of the cartridge 60 as appropriate) wherein the handles 65 may be formed in part or whole on the housing 22 instead of on the cartridge 60.

While the above-described embodiment describes an apparatus that is completely manually operated by a user, it is also possible to equip the apparatus with a motor for providing varying degrees of automated operation. Depending on where the motor is disposed (e.g., if the motor is disposed in part or in whole in the cartridge 60), it may be advantageous to employ the above-described magazine, so that the cartridge 60 need not be replaced merely for the purpose of refilling the liquid containers 31 or changing their contents. If a motor is included, then a controller may also be provided to control the motor, e.g., determining the times at which the cartridge 60 is rotated so that the emitted scent can be changed, etc. The controller could be operated directly by a user, and/or it could be operated via programs either designed by a user or preset during manufacture and selected by a user. The hardware and software, as well as any auxiliary features necessary or desirable, to implement such a system, would readily be understood by one of ordinary skill in the art. Examples of these aspects of the present invention are discussed in PCT Application No. PCT/US03/36090 (International Publication No. WO 2004/043502 A1), noted above.

In addition, while in the above-described embodiment the apparatus 20 is powered by a battery, it is also possible to arrange the apparatus so that electric power is supplied by an AC power supply. The components and configurations necessary and desirable to implement such an arrangement would readily be understood by one of ordinary skill in the art.

While in the above-described embodiment the electromechanical dispenser is a piezoelectrically actuated vibratory type liquid atomization apparatus, the dispenser could also be designed to employ a different type of dispensing mechanism.

Many different embodiments of the present invention may be constructed without departing from the spirit and scope of the present invention. It should be understood that the present invention is not limited to the specific embodiments described in this specification. To the contrary, the present invention is intended to cover various modifications and equivalent arrangements included within the spirit and scope of the invention as hereafter claimed. The scope of the claims is to be accorded the broadest interpretation so as to encompass all such modifications, equivalent structures and functions.

INDUSTRIAL APPLICABILITY

The embodiments described herein provide an apparatus capable of dispensing any of a plurality of volatile substances with operational flexibility in a user-friendly format, the apparatus being equipped with a single dispensing mechanism, whereby manufacturing costs may be reduced.

What is claimed is:

1. An apparatus for dispensing a volatile substance, comprising:
   an electromechanical dispenser for dispensing a volatile substance;
   a cartridge for holding a plurality of reservoirs, each reservoir for containing a volatile substance to be dispensed, said cartridge being rotatable so as to be able to position any one of said reservoirs in an engagement position in which said one reservoir can be engaged with said dispenser in such a manner that the volatile substance in said one reservoir can be dispensed; and
   a pivot arm for alternately disengaging a reservoir from said dispenser and engaging a successive reservoir with said dispenser during rotation of said cartridge.

2. An apparatus for dispensing a volatile substance according to claim 1, wherein said pivot arm maintains a state of disengagement between said dispenser and said reservoirs, during rotation of said cartridge from one engagement position to a subsequent engagement position.

3. An apparatus for dispensing a volatile substance according to claim 1, wherein said cartridge comprises a cam feature such that, when said cartridge is rotated so as to position any given reservoir in the engagement position, said pivot arm operates to engage said dispenser with the given reservoir, and when said cartridge is rotated so as to position the given reservoir out of the engagement position, said pivot arm operates to disengage said dispenser from the given reservoir.

4. An apparatus for dispensing a volatile substance according to claim 3,
   wherein said cam feature comprises a cut-away tubular portion having on a longitudinal end thereof a circumferential cross-sectional surface that alternately rises and falls along the circumference, and
   wherein said pivot arm is connected to said dispenser and said pivot arm abuts said circumferential cross-sectional surface of said cut-away tubular portion such that, when said cartridge rotates, said pivot arm alternately rises and falls, whereby said cam feature and said pivot arm operate to cause said dispenser to alternately disengage from and engage successive reservoirs.

5. An apparatus for dispensing a volatile substance according to claim 4,
   wherein each of said reservoirs is provided with a respective liquid delivery member, and
   wherein, by virtue of said alternately rising and falling circumferential cross-sectional surface, said dispenser is maintained at a position above the liquid delivery member of a next-to-be engaged reservoir, before said dispenser engages the next-to-be engaged reservoir, and said dispenser drops down upon the liquid delivery member to engage the next-to-be engaged reservoir, whereby collision, improper engagement and non-engagement between said dispenser and said liquid delivery member, due to vertical misalignment therebetween, are prevented.

6. An apparatus for dispensing a volatile substance according to claim 5, wherein each of said liquid delivery members is a wick.

7. An apparatus for dispensing a volatile substance according to claim 1, further comprising a housing, said housing comprising retention snaps for removably retaining said cartridge in said housing in such a manner as to permit rotation of said cartridge.

8. An apparatus for dispensing a volatile substance according to claim 1, further comprising:
   a housing, said housing having a circumferential surface provided with at least one concave portion; and
   at least one handle for rotating said cartridge, said at least one handle being provided on said cartridge, and said at least one handle being provided with a convex portion that fits into said concave portion,
   wherein, as said cartridge is rotated, said convex portion is rotationally brought into alignment with said concave portion at the same time as one of said reservoirs is brought into the engagement position in which said one reservoir can be engaged with said dispenser in such a manner that the volatile substance in said one reservoir can be dispensed, whereby the aligning of said convex portion with said concave portion provides visual, auditory and/or tactile feedback to a user of said apparatus that one of said reservoirs is in the engagement position in which said one reservoir can be engaged with said dispenser in such a manner that the volatile substance in said one reservoir can be dispensed.

9. An apparatus for dispensing a volatile substance according to claim 1, further comprising an exit port for releasing a volatile substance from said apparatus to the atmosphere outside of said apparatus.

10. An apparatus for dispensing a volatile substance according to claim 1, further comprising an adjustment lever for adjusting the amount of a volatile substance dispensed, the frequency of dispensing periods, and/or the duration of the dispensing periods.

11. An apparatus for dispensing a volatile substance according to claim 8, further comprising at least one of (a) an exit port for releasing a volatile substance from said apparatus to the atmosphere outside of said apparatus, and (b) an adjustment lever for adjusting the amount of a volatile substance dispensed, the frequency of dispensing periods, and/or the duration of the dispensing periods,
wherein at least one of said exit port and said adjustment lever is disposed in alignment, along a circumference of said housing, with said dispenser and with one of said concave portions.

12. A device for atomizing liquids, comprising:
an atomizer assembly comprising an atomization plate and a piezoelectric actuator coupled with said atomization plate to vibrate said atomization plate, thereby atomizing liquid supplied to said atomization plate;
a cartridge for holding a plurality of reservoirs, each reservoir for containing a liquid to be atomized, said cartridge being rotatable so as to be able to position any one of said reservoirs in an engagement position in which said one reservoir can be engaged with said atomizer assembly in such a manner that the liquid in said one reservoir can be supplied to said atomization plate; and
a pivot arm for alternately disengaging a reservoir from said atomizer assembly and engaging a successive reservoir with said atomizer assembly during rotation of said cartridge.

13. A device for atomizing liquids according to claim 12, wherein said pivot arm maintains a state of disengagement between said atomizer assembly and said reservoirs, during rotation of said cartridge from one engagement position to a subsequent engagement position.

14. A device for atomizing liquids according to claim 12, wherein said cartridge comprises a cam feature such that, when said cartridge is rotated so as to position any given reservoir in the engagement position, said pivot arm operates to engage said atomizer assembly with the given reservoir, and when said cartridge is rotated so as to position the given reservoir out of the engagement position, said pivot arm operates to disengage said atomizer assembly from the given reservoir.

15. A device for atomizing liquids according to claim 14,
wherein said cam feature comprises a cut-away tubular portion having on a longitudinal end thereof a circumferential cross-sectional surface that alternately rises and falls along the circumference, and
wherein said pivot arm is connected to said atomizer assembly and said pivot arm abuts said circumferential cross-sectional surface of said cut-away tubular portion such that, when said cartridge rotates, said pivot arm alternately rises and falls, whereby said cam feature and said pivot arm operate to cause said atomizer assembly to alternately disengage from and engage successive reservoirs.

16. A device for atomizing liquids according to claim 15,
wherein each of said reservoirs is provided with a respective liquid delivery member, and
wherein, by virtue of said alternately rising and falling circumferential cross-sectional surface, said atomizer assembly is maintained at a position above the liquid delivery member of a next-to-be engaged reservoir, before said atomizer assembly engages the next-to-be engaged reservoir, and said atomizer assembly drops down upon the liquid delivery member to engage the next-to-be engaged reservoir, whereby collision, improper engagement and non-engagement between said atomizer assembly and said liquid delivery member, due to vertical misalignment therebetween, are prevented.

17. A device for atomizing liquids according to claim 16, wherein each of said liquid delivery members is a wick.

18. A device for atomizing liquids according to claim 12, further comprising a housing, said housing comprising retention snaps for removably retaining said cartridge in said housing in such a manner as to permit rotation of said cartridge.

19. A device for atomizing liquids according to claim 12, further comprising:
a housing, said housing having a circumferential surface provided with at least one concave portion; and
at least one handle for rotating said cartridge, said at least one handle being provided on said cartridge, and said at least one handle being provided with a convex portion that fits into said concave portion,
wherein, as said cartridge is rotated, said convex portion is rotationally brought into alignment with said concave portion at the same time as one of said reservoirs is brought into the engagement position in which said one reservoir can be engaged with said atomizer assembly in such a manner that the liquid in said one reservoir can be supplied to said atomization plate, whereby the aligning of said convex portion with said concave portion provides visual, auditory and/or tactile feedback to a user of said apparatus that one of said reservoirs is in the engagement position in which said one reservoir can be engaged with said atomizer assembly in such a manner that the liquid in said one reservoir can be supplied to said atomization plate.

20. A device for atomizing liquids according to claim 12, further comprising an exit port for releasing an atomized liquid from said device to the atmosphere outside of said device.

21. A device for atomizing liquids according to claim 12, further comprising an adjustment lever for adjusting the amount of an atomized liquid dispensed from said device, the frequency of dispensing periods, and/or the duration of the dispensing periods.

22. A device for atomizing liquids according to claim 19, further comprising at least one of (a) an exit port for releasing an atomized liquid from said device to the atmosphere outside of said device, and (b) an adjustment lever for adjusting the amount of an atomized liquid dispensed from said device, the frequency of dispensing periods, and/or the duration of the dispensing periods,
wherein at least one of said exit port and said adjustment lever is disposed in alignment, along a circumference of said housing, with said atomizer assembly and with one of said concave portions.

* * * * *